(12) United States Patent
Burns et al.

(10) Patent No.: US 10,113,178 B2
(45) Date of Patent: Oct. 30, 2018

(54) TRANSGENIC MAIZE EVENT MON 87419 AND METHODS OF USE THEREOF

(71) Applicant: Monsanto Technology LLC, St. Louis, MO (US)

(72) Inventors: Wen C. Burns, Chesterfield, MO (US); Michael E. Goley, St. Louis, MO (US); Jintai Huang, Chesterfield, MO (US); Melinda C. McCann, St. Louis, MO (US); Aihua Shao, St. Louis, MO (US); Oscar C. Sparks, St. Louis, MO (US); Martin A. Stoecker, St. Louis, MO (US); Liping Wei, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 686 days.

(21) Appl. No.: 14/643,650

(22) Filed: Mar. 10, 2015

(65) Prior Publication Data

US 2015/0267221 A1 Sep. 24, 2015

Related U.S. Application Data

(60) Provisional application No. 61/968,342, filed on Mar. 20, 2014.

(51) Int. Cl.
| | |
|---|---|
| *C07H 21/04* | (2006.01) |
| *C12Q 1/68* | (2018.01) |
| *C12N 15/82* | (2006.01) |
| *C12Q 1/6895* | (2018.01) |
| *A01N 37/40* | (2006.01) |
| *A01N 57/20* | (2006.01) |

(52) U.S. Cl.
CPC ......... *C12N 15/8274* (2013.01); *A01N 37/40* (2013.01); *A01N 57/20* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 5,850,019 A | 12/1998 | Maiti et al. | |
| 5,914,451 A | 6/1999 | Martinell et al. | |
| 7,022,896 B1 | 4/2006 | Weeks et al. | |
| 7,105,724 B2 | 9/2006 | Weeks et al. | |
| 7,166,771 B2 | 1/2007 | Eenennaam et al. | |
| 7,241,567 B2 | 7/2007 | Weyens et al. | |
| 7,288,643 B2 | 10/2007 | Barbour et al. | |
| 7,323,556 B2 | 1/2008 | Bing et al. | |
| 7,812,224 B2 | 10/2010 | Weeks et al. | |
| 7,838,729 B2 | 11/2010 | Feng et al. | |
| 7,851,670 B2 | 12/2010 | Wan et al. | |
| 7,855,326 B2 | 12/2010 | Feng et al. | |
| 7,884,262 B2 | 2/2011 | Clemente et al. | |
| 7,939,721 B2 | 5/2011 | Arnevik et al. | |
| 8,084,666 B2 | 12/2011 | Feng et al. | |
| 8,119,380 B2 | 2/2012 | Weeks et al. | |
| 8,207,092 B2 | 6/2012 | Bhatti et al. | |
| 8,420,888 B2 | 4/2013 | Feng et al. | |
| 8,501,407 B2 * | 8/2013 | Brinker | A23D 9/00 426/634 |
| 8,629,323 B2 | 1/2014 | Weeks et al. | |
| 8,629,328 B2 | 1/2014 | Feng et al. | |
| 8,735,661 B2 * | 5/2014 | Brinker | A01H 5/10 435/6.1 |
| RE44,971 E | 6/2014 | Wan et al. | |
| 8,754,011 B2 | 6/2014 | Bhatti et al. | |
| RE45,048 E | 7/2014 | Feng et al. | |
| 8,791,325 B2 | 7/2014 | Feng et al. | |
| 8,999,411 B2 | 4/2015 | Froman et al. | |
| 9,024,115 B2 | 5/2015 | Brinker et al. | |
| 9,062,316 B2 * | 6/2015 | Flasinski | C07K 14/415 |
| 2003/0115626 A1 | 6/2003 | Weeks et al. | |
| 2003/0135879 A1 | 7/2003 | Weeks et al. | |
| 2004/0117870 A1 | 6/2004 | Weyens et al. | |
| 2006/0059590 A1 | 3/2006 | Cerny et al. | |
| 2008/0015110 A1 | 1/2008 | Clemente et al. | |
| 2008/0119361 A1 * | 5/2008 | Feng | A01N 25/00 504/244 |
| 2008/0120739 A1 | 5/2008 | Wan et al. | |
| 2008/0166699 A1 | 7/2008 | Baley et al. | |
| 2008/0305952 A1 | 12/2008 | Arnevik et al. | |
| 2009/0029861 A1 | 1/2009 | Feng et al. | |
| 2009/0081760 A1 | 3/2009 | D'Ordine et al. | |
| 2009/0199308 A1 | 8/2009 | Duff et al. | |
| 2010/0323893 A1 | 12/2010 | Ikeda | |
| 2011/0067134 A1 * | 3/2011 | Brinker | A23D 9/00 800/260 |
| 2011/0067141 A1 | 3/2011 | Froman et al. | |
| 2011/0154523 A1 * | 6/2011 | Diehn | A01H 5/10 800/265 |
| 2011/0245080 A1 | 10/2011 | Arnevik et al. | |
| 2011/0302667 A1 | 12/2011 | Brown et al. | |
| 2012/0222153 A1 | 8/2012 | Cui et al. | |
| 2012/0246763 A1 | 9/2012 | Flasinski | |
| 2012/0255050 A1 * | 10/2012 | Brinker | A01H 5/10 800/260 |

(Continued)

FOREIGN PATENT DOCUMENTS

| | | |
|---|---|---|
| CL | 83-08 | 1/2008 |
| EP | 2118290 | 5/2013 |

(Continued)

OTHER PUBLICATIONS

Genbank Accession No. FN550388—*Zea mays* transgenic partial 35S RNA promoter and partial pat gene (submitted by Waiblinger et al. Jul 2009, retrieved on Jan. 31, 2018 from http://www.ncbi.nlm.nih.gov/nuccore/FN550388). (Year: 2009).*

(Continued)

*Primary Examiner* — Gary Benzion
*Assistant Examiner* — Olayinka A Oyeyemi
(74) *Attorney, Agent, or Firm* — Pamela J. Sisson; Dentons US LLP

(57) ABSTRACT

The invention provides recombinant DNA molecules that are unique to the maize MON 87419 event and transgenic maize plants, plant parts, seeds, cells, and agricultural products containing the MON 87419 event as well as methods of using and detecting the maize MON 87419 event. Transgenic maize plants containing the MON 87419 event exhibit tolerance to dicamba and glufosinate herbicides.

18 Claims, 1 Drawing Sheet

Specification includes a Sequence Listing.

(56) References Cited

U.S. PATENT DOCUMENTS

| | | | |
|---|---|---|---|
| 2013/0217130 A1 | 8/2013 | Feng et al. | |
| 2013/0217576 A1 | 8/2013 | Feng | |
| 2013/0244875 A1 | 9/2013 | Feng et al. | |
| 2014/0041075 A1 | 2/2014 | Brinker et al. | |
| 2014/0315717 A1 | 10/2014 | Bhatti et al. | |
| 2014/0373190 A1 | 12/2014 | Brown et al. | |
| 2015/0119248 A1 | 4/2015 | Brown et al. | |
| 2015/0218659 A1 | 8/2015 | Brinker et al. | |
| 2016/0319299 A1 | 11/2016 | Brinker et al. | |

FOREIGN PATENT DOCUMENTS

| | | |
|---|---|---|
| RU | 2187555 | 8/2002 |
| WO | WO 1996/031609 | 10/1996 |
| WO | WO 1998/045424 | 10/1998 |
| WO | WO 03/013224 A2 | 2/2003 |
| WO | WO 2004/072235 A2 | 8/2004 |
| WO | WO 2004/099447 | 11/2004 |
| WO | WO 2005/061720 | 7/2005 |
| WO | WO 2007/047016 | 4/2007 |
| WO | WO 2007/143690 | 12/2007 |
| WO | WO 2007/146706 A2 | 12/2007 |
| WO | WO 2008/051633 | 5/2008 |
| WO | WO 2008/105890 | 9/2008 |
| WO | WO 2009/085982 A1 | 7/2009 |
| WO | WO 2009/091518 | 7/2009 |
| WO | WO 2009/102873 | 8/2009 |
| WO | WO 2010/085705 | 7/2010 |
| WO | WO 2011/034704 | 3/2011 |
| WO | WO 2011/066382 | 6/2011 |
| WO | WO 2012/134808 | 10/2012 |

OTHER PUBLICATIONS

Genbank Accession No. DQ156557—*Zea mays* transgenic phosphinothricin acetyltransferase gene, partial cds; and beta lactamase and phosphinothricin acetyltransferase genes, complete cds(submitted by Petit et al. Aug. 2005) (Year: 2005).*
Genbank Accession No. AY629235—*Zea mays* transgenic cultivar T25 phosphinothricin acetyltransferase (pat) gene, partial cds (submitted by Hernandez et al. May 2004, retrieved on Jan. 31, 2018 from http://www.ncbi.nlm.nih.gov/nuccore/AY629235). (Year: 2004).*
Genbank Accession No. EU363766—*Zea mays* Bt10 transgenic insert, (submitted by Milcamps et al. Dec. 2007, retrieved on Jan. 31, 2018 from http://www.ncbi.nlm.nih.gov/nuccore/EU363766). (Year: 2007).*
U.S. Appl. No. 14/745,241, filed Jun. 19, 2015, Brinker et al.
Alignment of SEQ ID No. 1 from U.S. Appl. No. 12/865,844 and SEQ ID Nos. 1 and 7 from U.S. Appl. No. 13/945,741, undated.
Alignment of SEQ ID No. 1 from U.S. Appl. No. 13/151,082 and SEQ ID NO. 1 from U.S. Appl. No. 13/945,741, undated.
Anklam et al., "Analytical methods for detection and determination of genetically modified organisms in agricultural crops and plant-derived food products," *Eur Food Res Technol*, 214:3-26, 2001.
Astaurov et al., *Great Soviet Encyclopedia* (in Russian), article "Biology," 1970.
Bartsch et al., "Initial steps in the degradation of phosphinothricin (glufosinate) by soil bacteria," *Appl Environ Microbiol*, 55(3):711-716, 1989.
Behrens et al., "Dicamba resistance: enlarging and preserving biotechnology-based weed management strategies," *Science*, 316:1185-1188, 2007.
Berdal et al., "Roundup Ready® soybean event-specific real-time quantitative PCR assay and estimation of the practical detection and quantification limits in GMO analyses," *Eur Food Res Technol* 213:432-438, 2001.
Bubner et al., "Use of real-time PCR for determining copy number and zygosity in transgenic plants," *Plant Cell Rep.*, 23:263-271, 2004.
Carter et al., "Evaluating weed control options in dicamba tolerant soybean," *North Central Weed Science Society Proc.*, Abstract and Poster, 63:25, 2008.
Carter et al., "Evaluation of dicamba tolerant soybean in Kentucky: a three-year review," Weed Science Society of America Annual Meeting, Denver, CO, Feb. 7-11, 2010.
Carter et al., "Resistant weed management using dicamba tolerant soybean," Weed Science Society of America Annual Meeting, Orlando, FL, Feb. 9-13, 2009.
Clarity herbicide EPA Reg. No. 7969-137, BASF, for use on dicamba-tolerant soybean MON 87708—grown for research, field trials, and seed production only, accepted with comments in EPA letter dated Feb. 13, 2008, Supplemental Label.
Clarity herbicide EPA Reg. No. 7969-137, BASF, for use on dicamba-tolerant soybean MON 87708—grown for seed production only, Feb. 26, 2009, Supplemental Label.
Clarity herbicide, EPA Reg. No. 7969-137, BASF, for use on dicamba-tolerant soybean MON 87708—grown for research, field trials, and seed production only, including USDA regulated plantings or seed production, accepted with comments in EPA letter dated May 28, 2010, Supplemental Label.
Coruzzi et al., "Tissue-specific and light-regulated expression of a pea nuclear gene encoding the small subunit of ribulose-1,5-bisphosphate carboxylase," *The EMBO Journal* 3(8):1671-1679, 1984.
Deblock et al., "Engineering herbicide resistance in plants by expression of a detoxifying enzyme," *EMBO J*, 6(9):2513-2518, 1987.
Doherty et al., "Palmer Amaranth control with dicamba and glufosinate as influenced by weed size and herbicide rate," *Summ of Arkansas Cotton Res*, 582:105-107, 2009.
English language translation of Chilean Application No. CL 83-08, filed Jan. 11, 2008.
English translation of p. 2 of Office Action issued in Ukrainian Application No. a 2012 04680, dated Jan. 26, 2015.
English translation of pp. 7-9 of Office Action issued in Russian Application No. 2012115127 dated Aug. 13, 2014.
GenBank Accession No. AY786443, dated Jun. 29, 2005.
GenBank Accession No. CW906303, dated Dec. 8, 2004.
GenBank Accession No. EI363554, dated Feb. 16, 2007.
Gruzdev, "Chemical protection of plants," *Agropromizdat* (in Russian), 3rd edition, p. 316, 1987.
Hayes et al., "Glyphosate resistant horseweed control in dicamba-glyphosate resistant soybeans," *Southern Weed Science Society Proceedings*, 61:51, 2008, Abstract.
Herman et al., "A Three-component Dicamba O-Demethylase from Pseudomonas maltophilia, Strain DI-6," *The Journal of Biological Chemistry* 280(26):24759-24767, 2005.
Hérouet et al., "Safety evaluation of the phosphinothricin acetyltransferase proteins encoded by the pat and bar sequences that confer tolerance to glufosinate-ammonium herbicide in transgenic plants," *Regulatory Toxicol and Pharmacol*, 41:134-149, 2005.
Hohe et al. "A tool for understanding homologous recombination in plants," *Plant Cell Rep.* 21:1135-1142, 2003.
International Preliminary Report on Patentability PCT/US2007/070517 (WO2007-143690), dated Dec. 10, 2008.
International Preliminary Report on Patentability PCT/US2009/033930 (WO2009-102873), dated Aug. 17, 2010.
International Preliminary Report on Patentability PCT/US2010/046759 (WO2011-034704), dated May 3, 2012.
Krueger et al., Isolation and identification of microorganisms for the degradation of dicamba, *J Agric Food Chem*, 37:534-538, 1989.
New England BioLabs Inc., 1998/99 Catalog, Nucleic Acids, Linkers and Primers, pp. 121 and 284.
Organization for Economic Co-operation and Development, "Consensus document on general information concerning the genes and their enzymes that confer tolerance to phosphinothricin herbicide," OECD Environmental Health and Safety Publications, Series on Harmonization of Regulatory Oversight of Biotechnology, No. 11. 1-26. Jun. 1, 1999.
Prohorov et al., *Grand Soviet Encyclopedia* (in Russian), 16:233, 1974.
Roche, *PCR Methods Manual, 3rd Edition*, p. 199, 2006.

(56) References Cited

OTHER PUBLICATIONS

Rychik et al., "A computer program for choosing optimal oligonucleotides for filter hybridization, sequencing and in vitro amplification of DNA," *Nucleic Acids Res.*, 17(21):8543-51, 1989.

Sequence alignment information as indicated in transmittal letter of Nov. 25, 2013 Information Disclosure Statement for U.S. Appl. No. 13/945,741.

Steckel et al., "Glyphosate-resistant horseweed control in dicamba glyphosate resistant soybeans," *North Central Weed Science Society Proc.*, 63:92, 2008.

Steckel et al., "Glyphosate-resistant horseweed control in soybean tolerant to both dicamba and glyphosate," *North Central Weed Science Society Proceedings*, 62:178, 2007.

Subramanian et al., "Engineering dicamba selectivity in crops: a search for appropriate degradative enzymes(s)," *J Industr Microbiol Biotech*, 19:344-349, 1997.

Thompson et al., "Characterization of the herbicide-resistance gene bar from *Streptomyces hygroscopicus*," *EMBO J*, 6:2519-2523, 1987.

Wang et al., "A three-component enzyme system catalyzes the O demethylase of the herbicide dicamba in *Pseudomonas maltophilia* DI-6," *Appl Environ Microbiol*, 63(4):1623-1626, 1997.

Wang et al., "Characterization of Cellular and Enzymatic Degradation of Dicamba by *Pseudomonas maltophilia*, Strain DI-6," dissertation presented to the Faculty of the Graduate Collage at the University of Nebraska, 1996.

Weeks, "Engineering of Crops for Tolerance to Treatment with the Herbicide, Dicamba," ACS Symposium presentation, San Francisco, CA, Mar. 22, 2010.

Wehrman et al., "The similarities of bar and pat gene products make them equally applicable for plant engineers," *Nature Biotech*, 14:1274-1278, 1996.

Zimmermann et al., "Event Specific Transgene Detection in Bt11 Corn by Quantitative PCR at the Integration Site," *Lebensm.-Wiss. u.-Technol.*, 33(3):210-216, 2000.

Final Office Action regarding U.S. Appl. No. 11/801,114, dated Aug. 26, 2009.

U.S. Appl. No. 14/676,691, filed Apr. 1, 2015, Brinker et al.

U.S. Appl. No. 14/625,566, filed Feb. 18, 2015, Flasinski.

U.S. Appl. No. 14/686,602, filed Apr. 14, 2015, Flasinski.

Clarity herbicide Specimen Label, BASF, "For weed control in asparagus, conservation reserve programs, corn, cotton, fallow croplands, general farmstead (noncropland), sorghum, grass grown for seed, hay, proso millet, pasture, rangeland, small grains, sod farms and farmstead turf, soybean, and sugarcane," 2010.

York et al., "Response of Strip-tilled Cotton to Preplant Applications of Dicamba and 2,4-D," *The Journal of Cotton Science* 8:213-222, 2004.

International Search Report and Written Opinion regarding International Application No. PCT/US2015/019663, dated Aug. 12, 2015.

GenBank Accession No. FP015960.2, dated May 17, 2009.

Carrington et al., "Cap-Independent Enhancement of Translation by a Plant Potyvirus 5' Nontranslated Region," *Journal of Virology* 64(4):1590-1597, 1990.

English translation of Office Action regarding Japanese Patent Application No. 2014-235817, dated Dec. 8, 2016.

Yamauchi et al., Series "Food Science," *Soybean Science* 1(5):188-194, 1997.

European Extended Search Report regarding European Application No. 15764078, dated Oct. 19, 2017.

Cline, "Too many stacked crop trait genes?", available at http://westernfarmpress.com/print/1850, retrieved from the Internet on Oct. 10, 2017.

Que et al., "Trait stacking in transgenic crops: Challenges and opportunities," *GM Crops* 1:4(220-229), 2010.

\* cited by examiner

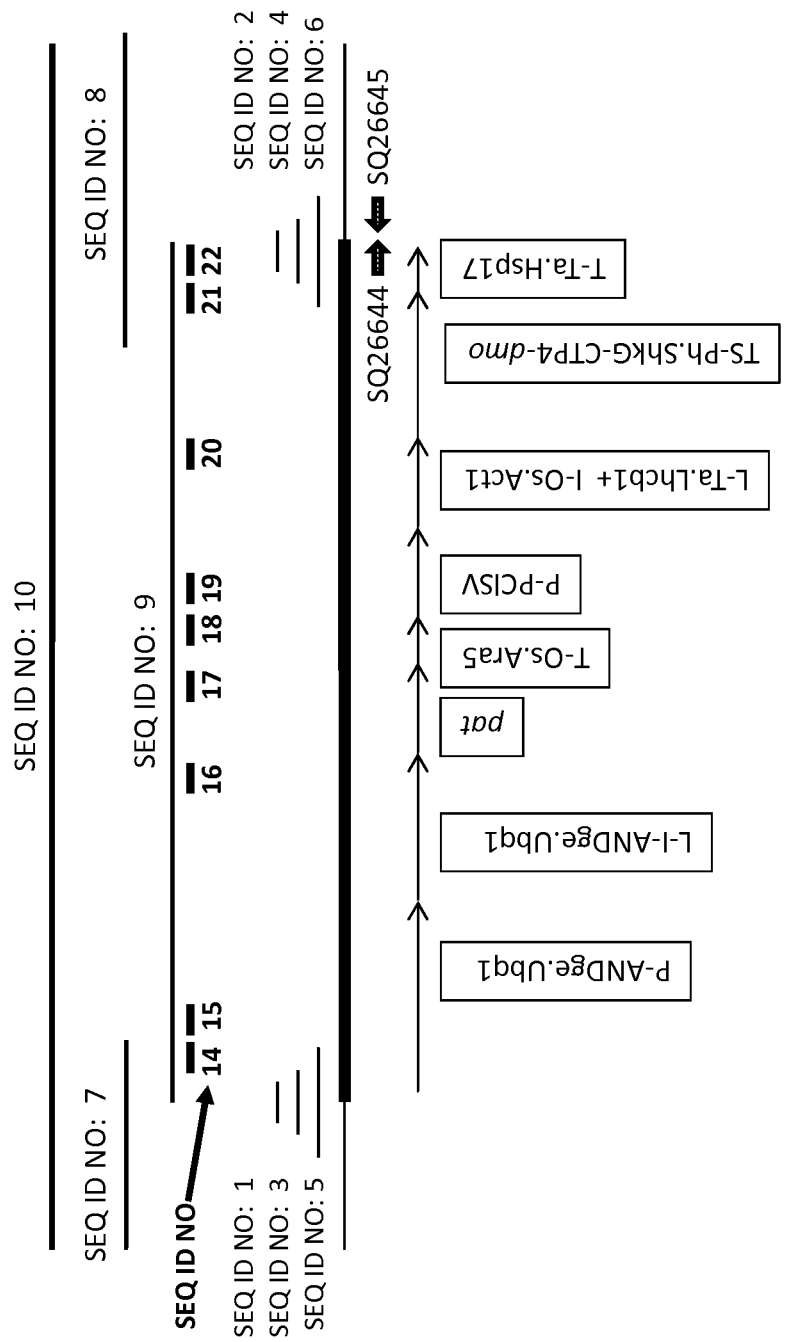

SEQUENCE LISTING

```
<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: Recombinant

<400> SEQUENCE: 1
caggtattga tgtgcgccag tcagcatcat                                    30

<210> SEQ ID NO 2
<211> LENGTH: 30
<212> TYPE: DNA
<213> ORGANISM: Artificial Sequence
<220> FEATURE:
<223> OTHER INFORMATION: Recombinant

<400> SEQUENCE: 2 ttcttttct ccatagcatt cgcaatacag                                     30

<210> SEQ ID NO 3
<211> LENGTH: 60
<212> TYPE: DNA
<213> ORGANISM: Artificial Sequence
<220> FEATURE:
<223> OTHER INFORMATION: Recombinant

<400> SEQUENCE: 3
gcaggcggtc gctgccaggt attgatgtgc gccagtcagc atcatcacac caaaagttag   60

<210> SEQ ID NO 4
<211> LENGTH: 60
<212> TYPE: DNA
<213> ORGANISM: Artificial Sequence
<220> FEATURE:
<223> OTHER INFORMATION: Recombinant

<400> SEQUENCE: 4
attggtaatt actctttctt tttctccata gcattcgcaa tacagttaga tgcgagtgaa   60

<210> SEQ ID NO 5
<211> LENGTH: 100
<212> TYPE: DNA
<213> ORGANISM: Artificial Sequence
<220> FEATURE:
<223> OTHER INFORMATION: Recombinant
```

```
<400> SEQUENCE: 5 agggggggggt tggcggggtg gcaggcggtc gctgccaggt attgatgtgc gccagtcagc        60
atcatcacac caaaagttag gcccgaatag tttgaaatta                              100

<210> SEQ ID NO 6
<211> LENGTH: 100
<212> TYPE: DNA
<213> ORGANISM: Artificial Sequence
<220> FEATURE:
<223> OTHER INFORMATION: Recombinant

<400> SEQUENCE: 6 cattttgaa ttgaaaaaaa attggtaatt actctttctt tttctccata gcattcgcaa         60
tacagttaga tgcgagtgaa gcacgataag tcacaaccat                              100

<210> SEQ ID NO 7
<211> LENGTH: 1771
<212> TYPE: DNA
<213> ORGANISM: Artificial Sequence
<220> FEATURE:
<223> OTHER INFORMATION: Recombinant

<400> SEQUENCE: 7
gttgatattt tgacccaaag acatgccatt ctcattgttt tcagttttat cctaccaatg        60
tagtaaccca aacagtttaa ttacaagtga atcaactgga aacaagatct acagactgca      120
cacagcacat taacaattct gcgccaaatg aatgacagag tgatttatag cactaagct       180 ggttttcatc atgaattttg atcagagcat aaaccttgtt gacaacagaa tagaatcaaa      240
caagctgctc agctcagatg gaccaaaata tgaacgcgc gcacagtata ttgaaccaaa       300
atagtgaacg cacagtagaa aacagacgga gaagctagtg cacactaaaa atagaactca      360
ctgatgcatt tttaaccgaa tcattaaaaa acagaccaac atgattagac cagctatcaa      420
aagacacact gctgagaatc aacaactgct atatgtgtga tctacctgaa ataaacagat      480 gcagttttt gtccctacag accaacatgt tttaatcaga atgccaatga taaatcctta      540
gagatctgga gagcaaacta attaaccact gagaatcaac aactgctata atccttagag      600
atctggagag cacactaatt aaccactgag cctctttggt cagcatgcag aaatccccaa      660
aactatactg taattcgaaa cccataagcg cacatcaaag caactccatt gttgatggtt      720
gggaatgtta aaaatatggt tgtggacacc aattgccgta acaaaccca cagggagaac       780 atgagtatga acaatcaaaa ctaacatgaa taagtggatg ttcagattaa gtaaggaaaa      840
tggtgcacag attaagaaca gagcaatgta tagcacaagt ggaaattaca aacctttttt      900
cacaaaatta caatctctag acagcacaca gcaagatctt ggaatggatg agggtgatga      960
atcggtgaaa aaagacagca cacagcaaga tctctagaac agaacatgaa atgttggaga     1020
gtggggatgg gttgtagacc taacctctgt ccatcctttt aatagccgtc gctgccaggt     1080
atggaatagg gcgccgtgag tgccgtcgag ggcgcgcgca ggggcgcggt ttggtgtggg     1140
cgggataccc ggcgcggtcg ggaaaccccca cggcggtcat cacggcgagc cgggggaggg     1200 ggggggttggc ggggtggcag gcggtcgctg ccaggtattg atgtgcgcca gtcagcatca     1260
tcacaccaaa agttaggccc gaatagtttg aaattagaaa gctcgcaatt gaggtctgtc     1320
gaggaggtta acctaggtac tgaattaccc tgttatccct aactagatat cgaattctaa     1380
ctataacggt cctaaggtag cgaatcgttc ttccttggcg ccaagacgc aaactcggac       1440 cggttcaagc cgtcaaggca cttctatgca accacagtca acttgaatgc cgcttgagtg     1500
```

```
ccttctcaag ttttttttttc ttgcaaaaat catttctttt ttttaaaaaa agtataattt    1560
ggatcgtgca aatttctctc taggtgtgtg tgtgactgtg tgagtaacaa tttctctagt    1620
tgtgcgcgac tgctgcttac tttggagatt acaatatctt tctaaaatgc ttcgattact    1680
tatttataaa ccgtctctaa ggccaattgc tcaagattca ttcaacaatt gaaacgtctc    1740
acatgattaa atcatataaa gtttctaagt c                                   1771

<210> SEQ ID NO 8
<211> LENGTH: 1767
<212> TYPE: DNA
<213> ORGANISM: Artificial Sequence
<220> FEATURE:
<223> OTHER INFORMATION: Recombinant

<400> SEQUENCE: 8
gcgagtctga tgagacatct ctgtattgtg tttctttccc cagtgttttc tgtacttgtg      60
taatcggcta atcgccaaca gattcggcga tgaataaatg agaaataaat tgttctgatt     120
ttgagtgcaa aaaaaaagga attagatctg tgtgtgtttt ttggatcccc ggggcggccg     180
cacaacaaac gaatacgtcc tgcttggcct actaggccaa cgcaggcgct ggccgtgacg     240
gccacgagcg aactgatatc gaattctagg gataacaggg taatccacgt gtagctaaac     300
gcgccctcat ctaagccccc atttggacgt gaatgtagac acgtcgaaat aaagatttcc     360
gaattagaat aatttgttta ttgctttcgc ctataaatac gacggatcgt aatttgtcgt     420
tttatcaaaa tgtactttca ttttataata acgctgcgga catctacatt tttgaattga     480
aaaaaaattg gtaattactc tttctttttc tccatagcat tcgcaataca gttagatgcg     540
agtgaagcac gataagtcac aaccataata catactatta gaatccggct ctttgccgag     600
tgcttttttt gggcactcgg caaagacttc tttaccggca aagtcctact ctcggtaacg     660
accacgttta ccgagagcag gacgctcggt acagggagac actcggcaaa gacctctttg     720
tcgagtgcca aacgctcggc aaagggccgt cagcagccgt ctatagcaga tgtttattat     780
ctttgccgag cgccaagcgt tggcactcgg caaacaagt gttgccgagt gcttaaattg     840
gacactcggc aaaatatatt tttctttttt cttttttgcaa ccaaactttc tgtggtttgt     900
tcctacacta tgtagacata catgttccat tttggcacaa ttataaaagt gtttgctata     960 aatattgat tttgttcgtt taattgaatt ttctcggata attcagattt gaactacaag    1020
tcactcaaaa aatggaaaac catgaatgca aaaatgatat ccatgttatt tagcacaagt    1080 tacgccgat tcaggagta gacccgaatt tttgagcacc atgctcacga acatgactg    1140 tgaacttgtc atccagttgt tttaaaattg tataaaacac aaacaaaatc aaaaaatcat    1200
gaaacttgtc cacatgtcat gatatcatca tatgtagagg ttgtgataaa agttgaaaa    1260 tatttcgtga agttgtcca tagttcactg agcctctttg tcgagtgtca cactcggcaa    1320
agcctttgtc gagtgcttca gacactcggc aaataagttg tttccagtag tgacattaat    1380
agaaaaagag tgcatagttc gttcacatag ctaactaatt ggttcattac aaagaaacat    1440
tagaacaagc ataatgatga cttggacata atgaaataaa atacataggt tgagggaacc    1500
aaacataatg gaacacagaa caaatagagg acaaacatcat agaaaacgac ataacttcac    1560
atgggtttta cgccaattgc tccacgccaa gtccataagt gctcgatgag atcatgttga    1620
agttggttgt atcatttgag actagtgatg ttgtggtggg agcatagcca ctctgtacga    1680
acttcaggga ttgtgatgag agatccacgt gcactccaat tgcggcaaac tcaacattac    1740
ttgcacgtgg gaccttgtcc tcgacaa                                      1767
```

<210> SEQ ID NO 9
<211> LENGTH: 6762
<212> TYPE: DNA
<213> ORGANISM: Artificial Sequence
<220> FEATURE:
<223> OTHER INFORMATION: Recombinant

<400> SEQUENCE: 9

```
gccagtcagc atcatcacac caaaagttag gcccgaatag tttgaaatta gaaagctcgc      60
aattgaggtc tgtcgaggag gttaacctag gtactgaatt accctgttat ccctaactag     120
atatcgaatt ctaactataa cggtcctaag gtagcgaatc gttcttcttg gcgcgccaag     180
acgcaaactc ggaccggttc aagccgtcaa ggcacttcta tgcaaccaca gtcaacttga     240
atgccgcttg agtgccttct caagtttttt tttcttgcaa aaatcatttc tttttttttaa    300 aaaaagtata atttggatcg tgcaaatttc tctctaggtg tgtgtgtgac tgtgtgagta     360
acaatttctc tagttgtgcg cgactgctgc ttactttgga gattacaata tctttctaaa    420
atgcttcgat tacttattta taaaccgtct ctaaggccaa ttgctcaaga ttcattcaac     480
aattgaaacg tctcacatga ttaaatcata taaagtttct aagtcttgtt tgacaagatt     540 ttttagatt ttcatctaaa ttggatgaaa ctatcaaaca ctaattttaa aaaatataag    600
agaagctccg gagataaaag gtcgtctatg ttattataag agtaaagtcg tctattctct     660
tcgtcccaac atatataatt ctaagcatga attgctttct ttttggacaa aaggagcatg     720
ccacaacaca agaatgatgt caccgtcatg cttggatcct tttatggtaa agcttcacct     780
tctataatct aacaatagag aaatcaggga aaaatcatgt tttggttgtt tttatttcta     840
acctccacaa taactttggt ttaccatttt ttgtttgatt ttagttttag agaagcgttt     900
ataacaggac ctaaaatctt ttttcagtac acagtacaac gcagacgctc atacacgcac     960
gcacactcac ctctatgaac acacgtaaga aaaccctaca ccttgagcac cttcgaagga    1020
ctgagccggt aaatatagag attctcgaag tcactattag cgcctcgttg tcaacgggaa    1080
tgtcgcttac cacttaaagc ataacgccga gaaatcccgt aataaatcca gtaaaatacg    1140
agcacccgtg ccaagttgaa tatttgaacc cgagtgggta gattccaccg caaaggacct    1200
aaccagatca tttcgcaaac aggaactaaa atcggtagag agcccagaca aaagcctttc    1260
ctaagagcca ctccagtgga agcccctact ttaggtataa aatgcaatac tagtgggggct   1320 cctaaataaa cttctatttt tcatggcctt ctaaaattca ctcccaaacc cctagctata    1380
gaagtctctt atccatcctc taaataaaaa tgggagtcta ttttatttca ccagagttga    1440
tcgtaaattt agtctctcaa attttataag ttgagggtag aggatgactg gagttgctct    1500
aaacggacct atcttcaagt gacctcagtg agcccgttta acggcgtcga caagtttaat    1560
ctaacggaca ccaaccagag aagagaacca ccgccagcgc cgagccaagc gacgttgaca    1620
tcttggcgcg gcacggcatc tccctggcgt ctggcccccct ctcgagactt ccgctccacc    1680
tcccaccggt ggcggtttcc aagtccgttc cgcctcctct cacacggcac gaaaccgtga    1740
cgggcaccgg cagcacgggg ggattccttt cccaccgctc cttcccttc ccttcctctc    1800 ccgccgctat aaatagccag ccccatcccc agcttctttc cccaacctca tcttctctcg    1860
tgttgttcgg cacaacccga tcgatcccca actccctcgt cgtctctcct cgcgagcctc    1920
gtcgatcccc cgcttcaagg tacggcgatc gattatcttc cctctctcta ccttctctct    1980 cttataggc ctgctagctc tgttcctgtt tttccatggc tgcgaggtac aatagatcgg     2040
cgatccatgg ttagggcctg ctagttgtgt tcctgttttt ccatggctgc gaggcacaat    2100
```

```
agatctgatg gcgttatgat ggttaacttg tcatactctt gcgatctatg gtcccttag      2160 gagtttagga catctattta atttcggata gttcgagatc tgtgatccat ggttagtacc      2220
ctaggcagtg gggttagatc cgtgctgtta tggttcgtag atggattctg attgctcagt      2280
aactgggaat cctgggatgg ttctagctgg ttcgcagata agatcgattt catgatatgc      2340
tatatcttgt ttggttgccg tggttccgtt aaatctgtct gttatgatct tagtctttga      2400
taaggttcgg tcgtgctagc tacgtcctgt gcagcactta attgtcaggt cataattttt      2460
agcatgcctt ttttttattg gtttggtttt gtctgactgg gctgtagata gtttcaatct      2520
ttgtctgact gggctgtaga tagtttcaat ctacctgtcg gttattttta ttaaatttgg      2580
atctgtatgt gtgtcatata tcttcatctt ttagatatat cgataggttt atatgttgct      2640
gtcggttttt tactgttcct ttatgagata tattcatgct tagatacatg aaacaacgtg      2700
ctgttacagt ttaatagttc ttgtttatct aataaacaaa taaggatagg tatatgctgc      2760
agttagtttt actggtactt tttttgacat gaacctacgg cttaataatt agtcttcatc      2820
aaataaaaag catatttttt aattatttcg atatacttga atgatgtcat atgcagcatc      2880
tgtgtgaatt tttggccctg tcttcatatg ctgtttattt gtttgggact gtttctttgg      2940
ttgataactc atcctgttgt ttggtgatcc ttttgcaggt gcaaccatgt ctccggagag      3000
gagaccagtt gagattaggc cagctacagc agctgatatg ccgcggtttt gtgatatcgt      3060
taaccattac attgagacgt ctacagtgaa ctttaggaca gagccacaaa caccacaaga      3120
gtggattgat gatctagaga ggttgcaaga tagatacct tggttggttg ctgaggttga      3180
gggtgttgtg ctggtattg cttacgctgg gccctggaag gctaggaacg cttacgattg      3240
gacagttgag agtactgttt acgtgtcaca taggcatcaa aggttgggcc taggatccac      3300
attgtacaca catttgctta agtctatgga ggcgcaaggt tttaagtctg tggttgctgt      3360
tataggcctt ccaaacgatc catctgttag gttgcatgag gctttgggat acacagcccg      3420
gggtacattg cgcgcagctg gatacaagca tggtggatgg catgatgttg gttttggca      3480 aagggatttt gagttgccag ctcctccaag gccagttagg ccagttaccc agatctgatt      3540
aattaactag gctactgtag ctagctgtgc atgtatgtgg tgtggttact aaaataatta      3600
gtgttttcct tttgtttgga agcatatgtg tggtgaataa atgatgaact ccgatgttcc      3660
tctctataaa tcttgatgat tcgctagcta tccgtacgtc gttgttcttt gatttgatga      3720
tgagattgaa aaatggaatg tcatgctaag gagggtgccg cggcccggcc gtgacggcca      3780
cgagcgaact cctgcaggac aacggagcag cctcctcagc aaatcctacc acctcattta      3840
aatagagtga ggttgatttg ctgaggtagc ggccgcgtta acaagcttct gcagaattcg      3900
tcaacgagat cttgagccaa tcaaagagga gtgatgtaga cctaaagcaa taatggagcc      3960
atgacgtaag ggcttacgcc catacgaaat aattaaaggc tgatgtgacc tgtcggtctc      4020
tcagaacctt tactttttat gtttggcgtg tattttaaa tttccacggc aatgacgatg      4080
tgacccaacg agatcttgag ccaatcaaag aggagtgatg tagacctaaa gcaataatgg      4140
agccatgacg taagggctta cgcccatacg aaataattaa aggctgatgt gacctgtcgg      4200
tctctcagaa cctttacttt ttatatttgg cgtgtatttt taaatttcca cggcaatgac      4260
gatgtgacct gtgcatccgc tttgcctata aataagtttt agtttgtatt gatcgacacg      4320
gtcgagaaga cacggccatt ctagaaccat cttccacaca ctcaagccac actattggag      4380
aacacacagg gacaacacac cataagatcc aagggaggcc tccgccgccg ccggtaacca      4440
```

```
ccccgcccct ctcctctttc tttctccgtt ttttttttccg tctcggtctc gatctttggc   4500
cttggtagtt tgggtgggcg agaggcggct tcgtgcgcgc ccagatcggt gcgcgggagg   4560
ggcgggatct cgcggctggg gctctcgccg gcgtggatcc ggcccggatc tcgcggggaa   4620
tggggctctc ggatgtagat ctgcgatccg ccgttgttgg gggagatgat gggggggttta  4680
aaatttccgc cgtgctaaac aagatcagga agaggggaaa agggcactat ggtttatatt   4740
tttatatatt tctgctgctt cgtcaggctt agatgtgcta gatctttctt tcttcttttt   4800
gtgggtagaa tttgaatccc tcagcattgt tcatcggtag ttttctttt catgatttgt    4860
gacaaatgca gcctcgtgcg gagcttttt gtaggtagaa gtgatcaacc atggcccaga    4920
tcaacaacat ggcccagggc atccagaccc tgaaccctaa ctctaacttc cacaagccgc   4980
aagtgcccaa gtctagctcc ttcctcgtgt tcggctccaa gaagctcaag aatagcgcca   5040
attccatgct ggtcctgaag aaagactcga tcttcatgca gaagttctgc tcctttcgca   5100
tcagtgcttc ggttgcgact gcctgcatgc tcaccttcgt taggaacgcc tggtacgtcg   5160
ccgctctccc tgaggagctg agcgagaagc ccttgggtcg caccatccta gacactccgt   5220
tagcccttta ccgccagcct gacggcgtag tggcggccct gcttgacatc tgcccgcata   5280
ggttcgctcc gctcagcgac ggcatcctcg tcaacgggca tcttcagtgc ccgtaccacg   5340
ggctggaatt tgacggcggt gggcagtgtg tccacaaccc gcacggcaac ggcgcacggc   5400
cagcttccct caacgttagg tcgttccctg ttgtcgagcg cgacgcactg atctggatct   5460
ggcctggcga cccagctctg gccgatccag gagccattcc cgacttcggt tgccgcgtgg   5520
acccagccta tcggacggtc ggcggttacg ggcacgtcga ttgtaactat aagctccttg   5580
tggacaacct tatggatttg ggccacgctc agtacgtgca ccgggctaac gctcagactg   5640
acgcctttga ccgtctcgaa agggaggtca tcgtcggcga cggagagatt caggcgctga   5700
tgaagatccc tggaggcacg ccctctgtgc tcatggcgaa gtttctcaga ggcgcgaaca   5760
cgcccgtgga cgcctggaac gacatccgct ggaataaggt ctccgcgatg ctgaacttca   5820
tcgccgttgc gcccgagggc acacccaaag agcagtcaat ccacagcaga gggacccata   5880
ttcttacacc ggaaaccgag gctagttgcc actacttctt cggctcgtca cggaatttcg   5940
ggatagacga tccggagatg gacggtgttc ttcgatcttg gcaagcgcaa gctctcgtca   6000
aggaagataa ggtggtcgtg gaggctatcg agcgtaggcg cgcctacgtt gaggcgaacg   6060
gtattaggcc cgcgatgctg tcctgcgacg aggccgcagt tagagtgtcg cgcgagatag   6120
aaaagctgga gcagctagag gccgcctgag gtaccgagct cgtcaatcac tagtgaattc   6180
tgcatgcgtt tggacgtatg ctcattcagg ttggagccaa tttggttgat gtgtgtgcga   6240
gttcttgcga gtctgatgag acatctctgt attgtgtttc ttttcccagt gttttctgta   6300
cttgtgtaat cggctaatcg ccaacagatt cggcgatgaa taaatgagaa ataaattgtt   6360
ctgattttga gtgcaaaaaa aaaggaatta gatctgtgtg tgttttttgg atccccgggg   6420
cggccgcaca acaaacgaat acgtcctgct tggcctacta ggccaacgca ggcgctggcc   6480
gtgacggcca cgagcgaact gatatcgaat tctaggata acagggtaat ccacgtgtag    6540
ctaaacgcgc cctcatctaa gccccatttt ggacgtgaat gtagacacgt cgaaataaag   6600
atttccgaat tagaataatt tgtttattgc tttcgcctat aaatacgacg gatcgtaatt   6660
tgtcgtttta tcaaaatgta ctttcatttt ataataacgc tgcggacatc tacatttttg   6720
aattgaaaaa aaattggtaa ttactctttc tttttctcca ta                     6762
```

<210> SEQ ID NO 10
<211> LENGTH: 9259
<212> TYPE: DNA
<213> ORGANISM: Artificial Sequence
<220> FEATURE:
<223> OTHER INFORMATION: Recombinant

<400> SEQUENCE: 10

```
gttgatattt tgacccaaag acatgccatt ctcattgttt tcagttttat cctaccaatg      60
tagtaaccca aacagtttaa ttacaagtga atcaactgga aacaagatct acagactgca     120
cacagcacat taacaattct gcgccaaatg aatgacagag tgatttatag cactaagct      180
ggttttcatc atgaattttg atcagagcat aaaccttgtt gacaacagaa tagaatcaaa     240
caagctgctc agctcagatg gaccaaaata tgaacgcgc gcacagtata ttgaaccaaa      300
atagtgaacg cacagtagaa aacagacgga gaagctagtg cacactaaaa atagaactca     360
ctgatgcatt tttaaccgaa tcattaaaaa acagaccaac atgattagac cagctatcaa     420
aagacacact gctgagaatc aacaactgct atatgtgtga tctacctgaa ataaacagat     480
gcagttttt gtccctacag accaacatgt tttaatcaga atgccaatga taaatcctta      540
gagatctgga gagcaaacta attaaccact gagaatcaac aactgctata atccttagag     600
atctggagag cacactaatt aaccactgag cctctttggt cagcatgcag aaatccccaa     660
aactatactg taattcgaaa cccataagcg cacatcaaag caactccatt gttgatggtt     720
gggaatgtta aaaatatggt tgtggacacc aattgccgta acaaaccca cagggagaac      780
atgagtatga acaatcaaaa ctaacatgaa taagtggatg ttcagattaa gtaaggaaaa     840
tggtgcacag attaagaaca gagcaatgta tagcacaagt ggaaattaca aaccttttt      900
cacaaaatta caatctctag acagcacaca gcaagatctt ggaatggatg agggtgatga     960
atcggtgaaa aagacagca cacagcaaga tctctagaac agaacatgaa atgttggaga    1020
gtggggatgg gttgtagacc taacctctgt ccatcctttt aatagccgtc gctgccaggt    1080
atggaatagg gcgccgtgag tgccgtcgag ggcgcgcgca ggggcgcggt ttggtgtggg    1140
cgggataccc ggcgcggtcg ggaaacccca cggcggtcat cacggcgagc cggggagggg    1200
ggggggttggc ggggtggcag gcggtcgctg ccaggtattg atgtgcgcca gtcagcatca    1260
tcacaccaaa agttaggccc gaatagtttg aaattagaaa gctcgcaatt gaggtctgtc    1320
gaggaggtta acctaggtac tgaattaccc tgttatccct aactagatat cgaattctaa    1380
ctataacggt cctaaggtag cgaatcgttc ttcttggcgc gccaagacgc aaactcggac    1440
cggttcaagc cgtcaaggca cttctatgca accacagtca acttgaatgc cgcttgagtg    1500
ccttctcaag ttttttttc ttgcaaaaat catttctttt ttttaaaaaa agtataattt     1560
ggatcgtgca aatttctctc taggtgtgtg tgtgactgtg tgagtaacaa tttctctagt    1620
tgtgcgcgac tgctgcttac tttggagatt acaatatctt tctaaaatgc ttcgattact    1680
tatttataaa ccgtctctaa ggccaattgc tcaagattca ttcaacaatt gaaacgtctc    1740
acatgattaa atcatataaa gtttctaagt cttgtttgac aagatttttt tagatttttca    1800
tctaaattgg atgaaactat caaacactaa ttttaaaaaa tataagagaa gctccggaga    1860
taaaaggtcg tctatgttat tataagagta aagtcgtcta ttctcttcgt cccaacatat    1920
ataattctaa gcatgaattg ctttcttttt ggacaaaagg agcatgccac aacacaagaa    1980
tgatgtcacc gtcatgcttg gatccttta tggtaaagct tcaccttcta taatctaaca    2040
atagagaaat cagggaaaaa tcatgttttg gttgttttta tttctaacct ccacaataac    2100
```

```
tttggtttac catttttttgt ttgattttag ttttagagaa gcgtttataa caggacctaa    2160
aatctttttt cagtacacag tacaacgcag acgctcatac acgcacgcac actcacctct    2220
atgaacacac gtaagaaaac cctacacctt gagcaccttc gaaggactga gccggtaaat    2280
atagagattc tcgaagtcac tattagcgcc tcgttgtcaa cgggaatgtc gcttaccact    2340
taaagcataa cgccgagaaa tcccgtaata aatccagtaa aatacgagca cccgtgccaa    2400
gttgaatatt tgaacccgag tgggtagatt ccaccgcaaa ggacctaacc agatcatttc    2460
gcaaacagga actaaaatcg gtagagagcc cagacaaaag cctttcctaa gagccactcc    2520
agtggaagcc cctactttag gtataaaatg caatactagt ggggctccta aataaacttc    2580
tatttttcat ggccttctaa aattcactcc caaaccccta gctatagaag tctcttatcc    2640
atcctctaaa taaaatgggg agtctatttt atttcaccag agttgatcgt aaatttagtc    2700
tctcaaattt tataagttga gggtagagga tgactggagt tgctctaaac ggacctatct    2760
tcaagtgacc tcagtgagcc cgtttaacgg cgtcgacaag tttaatctaa cggacaccaa    2820
ccagagaaga gaaccaccgc cagcgccgag ccaagcgacg ttgacatctt ggcgcggcac    2880
ggcatctccc tggcgtctgg cccccctctcg agacttccgc tccacctccc accggtggcg    2940
gtttccaagt ccgttccgcc tcctctcaca cggcacgaaa ccgtgacggg caccggcagc    3000
acggggggat tcctttccca ccgctccttc cctttccctt cctctcccgc cgctataaat    3060
agccagcccc atccccagct tctttcccca acctcatctt ctctcgtgtt gttcggcaca    3120
acccgatcga tccccaactc cctcgtcgtc tctcctcgcg agcctcgtcg atccccccgct   3180
tcaaggtacg gcgatcgatt atcttccctc tctctacctt ctctctctta tagggcctgc    3240
tagctctgtt cctgtttttc catggctgcg aggtacaata gatcggcgat ccatggttag    3300
ggcctgctag ttgtgttcct gttttttccat ggctgcgagg cacaatagat ctgatgcgt    3360
tatgatggtt aacttgtcat actcttgcga tctatggtcc ctttaggagt ttaggacatc    3420
tatttaattt cggatagttc gagatctgtg atccatggtt agtaccctag gcagtggggt    3480
tagatccgtg ctgttatggt tcgtagatgg attctgattg ctcagtaact gggaatcctg    3540
ggatggttct agctggttcg cagataagat cgatttcatg atatgctata tcttgtttgg    3600
ttgccgtggt tccgttaaat ctgtctgtta tgatcttagt cttttgataag gttcggtcgt   3660
gctagctacg tcctgtgcag cacttaattg tcaggtcata attttttagca tgccttttt    3720
ttattggttt ggttttgtct gactgggctg tagatagttt caatctttgt ctgactgggc    3780
tgtagatagt ttcaatctac ctgtcggttt attttattaa atttggatct gtatgtgtgt    3840
catatatctt catcttttag atatatcgat aggtttatat gttgctgtcg gttttttact    3900
gttcctttat gagatatatt catgcttaga tacatgaaac aacgtgctgt tacagtttaa    3960
tagttcttgt ttatctaata aacaaataag gataggtata tgctgcagtt agttttactg    4020
gtacttttt tgacatgaac ctacggctta ataattagtc ttcatcaaat aaaaagcata    4080
tttttttaatt atttcgatat acttgaatga tgtcatatgc agcatctgtg tgaattttg    4140
gccctgtctt catatgctgt ttatttgttt gggactgttt cttttggttga taactcatcc    4200
tgttgttgg tgatccttt gcaggtgcaa ccatgtctcc ggagaggaga ccagttgaga    4260
ttaggccagc tacagcagct gatatggccg cggtttgtga tatcgttaac cattacattg    4320
agacgtctac agtgaacttt aggacagagc cacaaacacc acaagagtgg attgatgatc    4380
tagagaggtt gcaagataga tacccttggt tggttgctga ggttgagggt gttgtggctg    4440
gtattgctta cgctgggccc tggaaggcta ggaacgctta cgattggaca gttgagagta    4500
```

```
ctgtttacgt gtcacatagg catcaaaggt tgggcctagg atccacattg tacacacatt    4560
tgcttaagtc tatggaggcg caaggtttta agtctgtggt tgctgttata ggccttccaa    4620
acgatccatc tgttaggttg catgaggctt tgggatacac agcccggggt acattgcgcg    4680
cagctggata caagcatggt ggatggcatg atgttggttt ttggcaaagg gattttgagt    4740
tgccagctcc tccaaggcca gttaggccag ttacccagat ctgattaatt aactaggcta    4800
ctgtagctag ctgtgcatgt atgtggtgtg gttactaaaa taattagtgt tttccttttg    4860
tttggaagca tatgtgtggt gaataaatga tgaactccga tgttcctctc tataaatctt    4920
gatgattcgc tagctatccg tacgtcgttg ttctttgatt tgatgatgag attgaaaaat    4980
ggaatgtcat gctaaggagg gtgccgcggc ccggccgtga cggccacgag cgaactcctg    5040
caggacaacg gagcagcctc ctcagcaaat cctaccacct catttaaata gagtgaggtt    5100
gatttgctga ggtagcggcc gcgttaacaa gcttctgcag aattcgtcaa cgagatcttg    5160
agccaatcaa agaggagtga tgtagaccta aagcaataat ggagccatga cgtaagggct    5220
tacgcccata cgaaataatt aaaggctgat gtgacctgtc ggtctctcag aacctttact    5280
ttttatgttt ggcgtgtatt tttaaatttc cacggcaatg acgatgtgac ccaacgagat    5340
cttgagccaa tcaagagga gtgatgtaga cctaaagcaa taatggagcc atgacgtaag    5400
ggcttacgcc catacgaaat aattaaaggc tgatgtgacc tgtcggtctc tcagaacctt    5460 tacttttat atttggcgtg tattttaaa tttccacggc aatgacgatg tgacctgtgc    5520
atccgctttg cctataaata agttttagtt tgtattgatc gacacggtcg agaagacacg    5580
gccattctag aaccatcttc cacacactca agcacacta ttggagaaca cacagggaca    5640
acacaccata agatccaagg gaggcctccg ccgccgccgg taaccacccc gcccctctcc    5700
tctttctttc tccgtttttt tttccgtctc ggtctcgatc tttggccttg gtagtttggg    5760
tgggcgagag gcggcttcgt gcgcgcccag atcggtgcgc gggaggggcg ggatctcgcg    5820 gctgggctc tcgccggcgt ggatccggcc cggatctcgc ggggaatggg gctctcggat    5880
gtagatctgc gatccgccgt tgttggggga gatgatgggg ggtttaaaat ttccgccgtg    5940
ctaaacaaga tcaggaagag gggaaaaggg cactatggtt tatatttta tatatttctg    6000 ctgcttcgtc aggcttagat gtgctagatc ttttctttctt cttttttgtgg gtagaatttg    6060 aatccctcag cattgttcat cggtagtttt tcttttcatg atttgtgaca aatgcagcct    6120
cgtgcggagc tttttttgtag gtagaagtga tcaaccatgg cccagatcaa caacatggcc    6180
cagggcatcc agaccctgaa ccctaactct aacttccaca agccgcaagt gcccaagtct    6240
agctccttcc tcgtgttcgg ctccaagaag ctcaagaata gcgccaattc catgctggtc    6300
ctgaagaaag actcgatctt catgcagaag ttctgctcct ttcgcatcag tgcttcggtt    6360
gcgactgcct gcatgctcac cttcgttagg aacgcctggt acgtcgccgc tctccctgag    6420
gagctgagcg agaagccctt gggtcgcacc atcctagaca ctccgttagc cctttaccgc    6480
cagcctgacg gcgtagtggc ggccctgctt gacatctgcc cgcataggtt cgctccgctc    6540
agcgacggca tcctcgtcaa cgggcatctt cagtgcccgt accacgggct ggaatttgac    6600
ggcggtgggg agtgtgtcca caacccgcac ggcaacggcg cacggccagc ttccctcaac    6660
gttaggtcgt tccctgttgt cgagcgcgac gcactgatct ggatctggcc tggcgaccca    6720
gctctggccg atccaggagc cattcccgac ttcggttgcc gcgtggaccc agcctatcgg    6780
acggtcggcg gttacgggca cgtcgattgt aactataagc tccttgtgga caaccttatg    6840
gatttgggcc acgctcagta cgtgcaccgg gctaacgctc agactgacgc ctttgaccgt    6900
```

```
ctcgaaaggg aggtcatcgt cggcgacgga gagattcagg cgctgatgaa gatccctgga    6960
ggcacgccct ctgtgctcat ggcgaagttt ctcagaggcg cgaacacgcc cgtggacgcc    7020
tggaacgaca tccgctggaa taaggtctcc gcgatgctga acttcatcgc cgttgcgccc    7080
gagggcacac ccaaagagca gtcaatccac agcagaggga cccatattct tacaccggaa    7140
accgaggcta gttgccacta cttcttcggc tcgtcacgga atttcgggat agacgatccg    7200
gagatggacg tgttcttccg atcttggcaa gcgcaagctc tcgtcaagga agataaggtg    7260
gtcgtggagg ctatcgagcg taggcgcgcc tacgttgagg cgaacggtat taggcccgcg    7320
atgctgtcct gcgacgaggc cgcagttaga gtgtcgcgcg agatagaaaa gctggagcag    7380
ctagaggccg cctgaggtac cgagctcgtc aatcactagt gaattctgca tgcgtttgga    7440
cgtatgctca ttcaggttgg agccaatttg gttgatgtgt gtgcgagttc ttgcgagtct    7500
gatgagacat ctctgtattg tgtttctttc cccagtgttt tctgtacttg tgtaatcggc    7560
taatcgccaa cagattcggc gatgaataaa tgagaaataa attgttctga ttttgagtgc    7620
aaaaaaaaag gaattagatc tgtgtgtgtt ttttggatcc ccggggcggc cgcacaacaa    7680
acgaatacgt cctgcttggc ctactaggcc aacgcaggcg ctggccgtga cggccacgag    7740
cgaactgata tcgaattcta gggataacag ggtaatccac gtgtagctaa acgcgccctc    7800
atctaagccc ccatttggac gtgaatgtag acacgtcgaa ataaagattt ccgaattaga    7860
ataatttgtt tattgctttc gcctataaat acgacggatc gtaatttgtc gttttatcaa    7920
aatgtacttt cattttataa taacgctgcg gacatctaca ttttgaatt gaaaaaaaat    7980
tggtaattac tctttctttt tctccatagc attcgcaata cagttagatg cgagtgaagc    8040
acgataagtc acaaccataa tacatactat tagaatccgg ctctttgccg agtgcttttt    8100
ttgggcactc ggcaaagact tctttaccgg caaagtccta ctctcggtaa cgaccacgtt    8160
taccgagagc aggacgctcg gtacagggag acactcggca aagacctctt tgtcgagtgc    8220
caaacgctcg gcaagggcc gtcagcagcc gtctatagca gatgtttatt atctttgccg    8280
agcgccaagc gttggcactc ggcaaaacaa gtgttgccga gtgcttaaat tggacactcg    8340
gcaaaatata tttttctttt ttcttttttgc aaccaaactt tctgtggttt gttcctacac    8400
tatgtagaca tacatgttcc attttggcac aattataaaa gtgtttgcta taaatattag    8460
atttttgttcg tttaattgaa ttttctcgga taattcagat ttgaactaca agtcactcaa    8520
aaaatggaaa accatgaatg caaaaatgat atccatgtta tttagcacaa gttacggccg    8580
atttcaggag tagacccgaa ttttttgagca ccatgctcac gaaacatgac tgtgaacttg    8640
tcatccagtt gttttaaaat tgtataaaac acaaacaaaa tcaaaaaatc atgaaacttg    8700
tccacatgtc atgatatcat catatgtaga ggttgtgata aaaagttgaa atatttcgt    8760
gaaagttgtc catagttcac tgagcctctt tgtcgagtgt cacactcggc aaagcctttg    8820
tcgagtgctt cagacactcg gcaaataagt tgtttccagt agtgacatta atagaaaaag    8880
agtgcatagt tcgttcacat agctaactaa ttggttcatt acaaagaaac attagaacaa    8940
gcataatgat gacttggaca taatgaaata aaatacatag gttgagggaa ccaaacataa    9000
tggaacacag aacaaataga ggacaacatc atagaaaacg acataacttc acatgggttt    9060
tacgccaatt gctccacgcc aagtccataa gtgctcgatg agatcatgtt gaagttggtt    9120
gtatcatttg agactagtga tgttgtggtg ggagcatagc cactctgtac gaacttcagg    9180
gattgtgatg agagatccac gtgcactcca attgcggcaa actcaacatt acttgcacgt    9240
gggaccttgt cctcgacaa                                                 9259
```

```
<210> SEQ ID NO 11
<211> LENGTH: 33
<212> TYPE: DNA
<213> ORGANISM: Artificial Sequence
<220> FEATURE:
<223> OTHER INFORMATION: Recombinant

<400> SEQUENCE: 11
gaattgaaaa aaaattggta attactcttt ctt                                    33

<210> SEQ ID NO 12
<211> LENGTH: 24
<212> TYPE: DNA
<213> ORGANISM: Artificial Sequence
<220> FEATURE:
<223> OTHER INFORMATION: Recombinant

<400> SEQUENCE: 12
atcgtgcttc actcgcatct aact                                              24

<210> SEQ ID NO 13
<211> LENGTH: 19
<212> TYPE: DNA
<213> ORGANISM: Artificial Sequence
<220> FEATURE:
<223> OTHER INFORMATION: Recombinant

<400> SEQUENCE: 13
ctccatagca ttcgcaata                                                    19

<210> SEQ ID NO 14
<211> LENGTH: 81
<212> TYPE: DNA
<213> ORGANISM: Artificial Sequence
<220> FEATURE:
<223> OTHER INFORMATION: Recombinant

<400> SEQUENCE: 14
attagaaagc tcgcaattga ggtctgtcga ggaggttaac ctaggtactg aattaccctg        60
ttatccctaa ctagatatcg a                                                 81

<210> SEQ ID NO 15
<211> LENGTH: 61
<212> TYPE: DNA
<213> ORGANISM: Artificial Sequence
<220> FEATURE:
<223> OTHER INFORMATION: Recombinant

<400> SEQUENCE: 15
tggcgcgcca agacgcaaac tcggaccggt tcaagccgtc aaggcacttc tatgcaacca        60
c                                                                       61

<210> SEQ ID NO 16
<211> LENGTH: 59
<212> TYPE: DNA
<213> ORGANISM: Artificial Sequence
<220> FEATURE:
<223> OTHER INFORMATION: Recombinant

<400> SEQUENCE: 16
atcctgttgt ttggtgatcc ttttgcaggt gcaaccatgt ctccggagag gagaccagt         59
```

```
<210> SEQ ID NO 17
<211> LENGTH: 56
<212> TYPE: DNA
<213> ORGANISM: Artificial Sequence
<220> FEATURE:
<223> OTHER INFORMATION: Recombinant

<400> SEQUENCE: 17
ccagttaggc cagttaccca gatctgatta attaactagg ctactgtagc tagctg          56

<210> SEQ ID NO 18
<211> LENGTH: 99
<212> TYPE: DNA
<213> ORGANISM: Artificial Sequence
<220> FEATURE:
<223> OTHER INFORMATION: Recombinant

<400> SEQUENCE: 18
aaaaatggaa tgtcatgcta aggagggtgc cgcggcccgg ccgtgacggc cacgagcgaa      60
ctcctgcagg acaacggagc agcctcctca gcaaatcct                             99

<210> SEQ ID NO 19
<211> LENGTH: 56
<212> TYPE: DNA
<213> ORGANISM: Artificial Sequence
<220> FEATURE:
<223> OTHER INFORMATION: Recombinant

<400> SEQUENCE: 19
tgaggttgat ttgctgaggt agcggccgcg ttaacaagct tctgcagaat tcgtca          56

<210> SEQ ID NO 20
<211> LENGTH: 55
<212> TYPE: DNA
<213> ORGANISM: Artificial Sequence
<220> FEATURE:
<223> OTHER INFORMATION: Recombinant

<400> SEQUENCE: 20
aggtagaagt gatcaaccat ggcccagatc aacaacatgg cccagggcat ccaga           55

<210> SEQ ID NO 21
<211> LENGTH: 91
<212> TYPE: DNA
<213> ORGANISM: Artificial Sequence
<220> FEATURE:
<223> OTHER INFORMATION: Recombinant

<400> SEQUENCE: 21
cgcgagatag aaaagctgga gcagctagag gccgcctgag gtaccgagct cgtcaatcac      60
tagtgaattc tgcatgcgtt tggacgtatg c                                     91

<210> SEQ ID NO 22
<211> LENGTH: 67
<212> TYPE: DNA
<213> ORGANISM: Artificial Sequence
<220> FEATURE:
<223> OTHER INFORMATION: Recombinant

<400> SEQUENCE: 22
ctagggataa cagggtaatc cacgtgtagc taaacgcgcc ctcatctaag cccccatttg      60
gacgtga                                                                67
```

TRANSGENIC MAIZE EVENT MON 87419 AND METHODS OF USE THEREOF

CROSS REFERENCE TO RELATED APPLICATIONS

This application claims the benefit of U.S. Provisional Application No. 61/968,342, filed Mar. 20, 2014, herein incorporated by reference in its entirety.

INCORPORATION OF SEQUENCE LISTING

The sequence listing that is contained in the file named "MONS362US.txt", which is 29.4 KB (measured in MS-Windows) and created on Mar. 9, 2015, is filed herewith and incorporated herein by reference in its entirety.

FIELD OF THE INVENTION

The invention relates to recombinant DNA molecules that are unique to the transgenic maize event MON 87419. The invention also relates to transgenic maize plants, parts, seeds, cells, and agricultural products containing the maize MON 87419 event as well as methods of using the same. Transgenic maize plants containing the maize MON 87419 event exhibit tolerance to dicamba and glufosinate herbicides.

BACKGROUND OF THE INVENTION

Maize (*Zea mays*) is an important crop in many areas of the world. The methods of biotechnology have been applied to this crop in order to produce maize with desirable traits. One such desirable trait is herbicide tolerance. Expression of a heterologous gene, also known as a transgene, for herbicide tolerance in a plant can confer herbicide tolerance on the plant. However, the expression of a transgene, and therefore its effectiveness, may be influenced by many different factors including the orientation and composition of the cassette driving expression of the individual transgene transferred to the plant chromosome and the chromosomal location and the genomic result of the transgene insertion. This is complicated further in transgenic plants with multiple molecularly-linked transgenes, each conferring a separate trait. In such a situation, proper expression of each of the molecularly-linked transgenes in the plant must result from the same transgene insertion (also called a multi-gene event). In such cases, it is necessary to design and test multiple expression cassettes, each with a different configuration of transgenes and expression elements, and then to produce and analyze a large number of individual plant transformation events through multiple generations of plants in order to select the transgenic event having superior properties relative to the each of the desirable traits and the optimal phenotypic and agricultural characteristics necessary to make it suitable for commercial purposes. Such selection requires extensive molecular characterization as well as greenhouse and field trials over multiple years, in multiple locations, and under a variety of conditions so that a significant amount of agronomic, phenotypic, and molecular data may be collected. The resulting data and observations must then be analyzed by teams of scientists and agronomists with the goal of selecting the event suitable for commercial agricultural use across a wide range of germplasm and in a variety of field conditions. Once selected, the commercial event conferring the desirable traits may be introgressed into other genetic backgrounds using plant breeding methods, thus producing a number of different crop varieties that contain the desirable trait and are suitably adapted to specific local growing conditions.

To make a transgenic plant containing a single transformation event, a portion of a recombinant DNA construct is transferred into the genome of a maize cell using plant transformation techniques. This maize cell is subsequently used to produce a unique $R_0$ plant, which can then be used to produce transgenic progeny plants. The genome of the progeny plants contains the unique event, and these plants can be tested for the desired trait(s) as well as for agronomic performance. The effectiveness of an event can be impacted by cis and/or trans factors relative to the integration site in the transformation event. The phenotype conferred by the event can also be impacted by the size and design of the DNA construct, which can vary by the combination of genetic elements in an expression cassette, number of transgenes, number of expression cassettes, and configuration of such elements and such cassettes. The performance of a given event can be further complicated by factors such as plant developmental, diurnal, temporal, or spatial patterns of transgene expression; or by extrinsic factors, for example, environmental plant growth conditions, water availability, nitrogen availability, heat, or stress. Thus, the ability to create an event conferring a desirable set of phenotypic traits is not readily predictable.

BRIEF SUMMARY OF THE INVENTION

The invention provides a recombinant DNA molecule containing a sequence selected from the group consisting of SEQ ID NO:1-10. The invention also provides a recombinant DNA derived from a transgenic maize plant or seed containing the maize MON 87419 event, a representative sample of seed comprising the maize MON 87419 event having been deposited as ATCC Accession No. PTA-120860. The invention also provides a recombinant DNA molecule that is an amplicon diagnostic for the presence of DNA derived from the maize MON 87419 event. The invention also provides a DNA molecule that is in a maize plant, cell, seed, progeny plant, or plant part derived from transgenic maize comprising the maize MON 87419 event.

The invention provides a DNA molecule having sufficient length of contiguous DNA sequence of SEQ ID NO:10 to function as a DNA probe that hybridizes under stringent hybridization conditions with a DNA molecule comprising a DNA sequence selected from the group consisting of SEQ ID NO:1-10 and does not hybridize under the stringent hybridization conditions with a DNA molecule not comprising a DNA sequence selected from the group consisting of SEQ ID NO:1-10. The invention also provides a pair of DNA molecules comprising a first DNA molecule and a second DNA molecule, wherein the first DNA molecule is a fragment of SEQ ID NO:9 and the second DNA molecule is a fragment of the maize genomic DNA of the maize MON 87419 event, and wherein the first and second DNA molecules each comprise a DNA sequence of sufficient length of contiguous nucleotides to function as DNA primers when used together in an amplification reaction with DNA containing the maize MON 87419 event to produce an amplicon diagnostic for the maize MON 87419 event in a sample.

The invention provides a method of detecting the presence of the maize MON 87419 event in a sample of DNA by contacting the sample with a DNA probe, subjecting the sample and the DNA probe to stringent hybridization conditions, and detecting hybridization of the DNA probe to a DNA molecule in the sample, where the hybridization of the DNA probe to the DNA molecule indicates the presence of the maize MON 87419 event in the sample of DNA.

The invention provides a method of detecting the presence of the maize MON 87419 event in a sample of DNA by contacting the sample with a pair of DNA primers, performing an amplification reaction sufficient to produce a DNA amplicon comprising a sequence selected from the group consisting of SEQ ID NO:1-8 and SEQ ID NO:10, and detecting the presence of the DNA amplicon in the reaction, wherein the presence of the DNA amplicon in the reaction indicates the presence of the maize MON 87419 event in the sample of DNA.

The invention provides a DNA detection kit containing at least one DNA molecule comprising a DNA sequence of sufficient length of contiguous nucleotides of SEQ ID NO:10 to function as a primer or probe specific for detecting the presence of the maize MON 87419 event in a sample of DNA.

The invention provides a recombinant maize plant, seed, cell, plant part, or commodity product comprising a DNA molecule having a DNA sequence selected from the group consisting of SEQ ID NO:1-10. The invention also provides a transgenic maize plant, seed, or cell that is tolerant to glufosinate or dicamba, or glufosinate and dicamba herbicides. The invention also provides a transgenic maize plant, seed, cell, plant part, or commodity product containing the maize MON 87419 event. The invention also provides a transgenic maize plant or seed that is a hybrid having at least one parent plant that comprised the maize MON 87419 event.

The invention provides a method for controlling weeds in an area comprising planting transgenic maize comprising the maize MON 87419 event in an area and applying an effective dose of dicamba or glufosinate or dicamba and glufosinate herbicides to control the weeds in the area without injuring the transgenic maize. The invention also provides a method for controlling weeds by applying an effective dose of glufosinate herbicide of about 0.1 pounds acid equivalent per acre to about 16 pounds acid equivalent per acre of glufosinate herbicide over a growing season. The invention also provides a method for controlling weeds by applying an effective dose of glufosinate herbicide of about 0.4 pounds acid equivalent per acre to about 1.59 pounds acid equivalent per acre of glufosinate herbicide over a growing season. The invention also provides a method for controlling weeds by applying an effective dose of dicamba herbicide of about 0.1 pounds acid equivalent per acre to about 16 pounds acid equivalent per acre of dicamba herbicide over a growing season. The invention also provides a method for controlling weeds by applying an effective dose of dicamba herbicide is about 0.5 pounds acid equivalent per acre to about 2 pounds acid equivalent per acre of dicamba herbicide over a growing season.

The invention provides a method of producing a transgenic maize plant that is tolerant to glufosinate and dicamba herbicides by sexually crossing a transgenic maize plant comprising the maize MON 87419 event with a second maize plant, collecting the seed produced, growing the seed to produce progeny plants, treating the progeny plants with glufosinate or dicamba, or glufosinate and dicamba herbicides, and selecting a progeny plant that is tolerant to glufosinate and dicamba herbicides. The invention also provides a method of producing a transgenic maize plant that is tolerant to glufosinate and dicamba herbicides by selfing a transgenic maize plant comprising the maize MON 87419 event, collecting the seed produced, growing the seed to produce progeny plants, treating the progeny plants with glufosinate or dicamba, or dicamba and glufosinate herbicides, and selecting a progeny plant that is tolerant to glufosinate and dicamba herbicides.

BRIEF DESCRIPTION OF THE DRAWINGS

FIG. 1: illustrates the organization of the transgene insert in the genome of a maize plant comprising maize event MON 87419. The horizontal lines correspond to the relative positions of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; the thick arrows labeled SQ26644 and SQ26645 represent the approximate position of a pair of primers used to identify transgenic maize containing the maize MON 87419 event; the thick, short lines numbered 14 through 22 represent the relative position of unique recombinant construct sequences within the DNA insert (SEQ ID NO:9) and the number refers to the corresponding SEQ ID NO of each, respectively; the thin horizontal arrows represent the relative organization of the two separate expression cassettes of the heterologous transgene inserted DNA of the maize MON 87419 event and the boxes indicate the separate elements of the two expression cassettes; a leading 'P' represents a promoter element, a leading 'L' represents a leader element, a leading 'I' represents an intron, a leading 'TS' represents a chloroplast transit peptide, a leading 'T' represents a 3' transcription termination and polyadenylation element (3' UTR), pat represents the coding region for the phosphinothricin acetyl transferase (PAT) protein, and dmo represents the coding region for the dicamba mono-oxygenase (DMO) protein.

BRIEF DESCRIPTION OF THE SEQUENCES

SEQ ID NO:1 is a thirty nucleotide DNA sequence representing the 5' junction of maize genomic DNA and the transgene insert. SEQ ID NO:1 corresponds to nucleotide positions 1232 to 1261 of SEQ ID NO:10.

SEQ ID NO:2 is a thirty nucleotide DNA sequence representing the 3' junction of maize genomic DNA and the transgene insert. SEQ ID NO:2 corresponds to nucleotide positions 7994 to 8023 of SEQ ID NO:10.

SEQ ID NO:3 is a sixty nucleotide DNA sequence representing the 5' junction of maize genomic DNA and the transgene insert. SEQ ID NO:3 corresponds to nucleotide positions 1217 to 1276 of SEQ ID NO:10.

SEQ ID NO:4 is a sixty nucleotide DNA sequence representing the 3' junction of maize genomic DNA and the transgene insert. SEQ ID NO:4 corresponds to nucleotide positions 7979 to 8038 of SEQ ID NO:10.

SEQ ID NO:5 is a one-hundred nucleotide DNA sequence representing the 5' junction of maize genomic DNA and the transgene insert. SEQ ID NO:5 corresponds to nucleotide positions 1197 to 1296 of SEQ ID NO:10.

SEQ ID NO:6 is a one-hundred nucleotide DNA sequence representing the 3' junction of maize genomic DNA and the transgene insert. SEQ ID NO:6 corresponds to nucleotide positions 7959 to 8058 of SEQ ID NO:10.

SEQ ID NO:7 is a 1771 nucleotide DNA sequence representing 1246 nucleotides of the 5' flanking maize genomic DNA and 525 nucleotides of the 5' end of the transgene insert.

SEQ ID NO:8 is a 1767 nucleotide DNA sequence representing 516 nucleotides of the 3' end of the transgene insert and 1251 nucleotides of the 3' flanking maize genomic DNA.

SEQ ID NO:9 is a 6762 nucleotide DNA sequence corresponding to the transgene insert of the maize MON 87419 event.

SEQ ID NO:10 is a 9259 nucleotide DNA sequence corresponding to the maize MON 87419 event; the sequence contains the 5' flanking genomic DNA sequence from positions 1 to 1246, the transgenic DNA insert from positions 1247 to 8008, and the 3' flanking genomic DNA sequence from positions 8009 to 9259.

SEQ ID NO:11 is a 33 nucleotide DNA sequence corresponding to a primer referred to as SQ26644 and used to identify maize MON 87419 event DNA in a sample; it corresponds to positions 7966 to 7998 of SEQ ID NO:10.

SEQ ID NO:12 is a 24 nucleotide DNA sequence corresponding to a primer referred to as SQ26645 and used to identify maize MON 87419 event DNA in a sample; it corresponds to positions 8022 to 8045 of SEQ ID NO:10.

SEQ ID NO:13 is a 19 nucleotide DNA sequence corresponding to a probe referred to as PB11207 and used to identify maize MON 87419 event DNA in a sample; it corresponds to positions 8002 to 8020 of SEQ ID NO:10.

SEQ ID NOs:14-22 are DNA sequences corresponding to unique sequences within the transgene insert of the maize MON 87419 event.

DETAILED DESCRIPTION OF THE INVENTION

The following definitions and methods are provided to better define the invention and to guide those of ordinary skill in the art in the practice of the invention. Unless otherwise noted, terms are to be understood according to conventional usage by those of ordinary skill in the relevant art.

Modern plant transformation techniques are used to generate genetically engineered plants. The term 'transgenic' may also be used to refer to genetically engineered plants. During the process of generating a transgenic plant, foreign DNA is randomly inserted into the genome of a plant cell. During the transformation procedure, many individual cells are transformed. Due to random integration, a separate and unique DNA recombination event will take place within the genome of each individual transformed plant cell. An entire transgenic plant is then generated from a single individual transgenic cell which necessarily results in every cell of the transgenic plant containing the uniquely inserted DNA as a stable part of its genome. The transgenic herbicide tolerant maize containing the maize MON 87419 event comprises a single insertion of transgenic DNA into the chromosome/genome of the maize germplasm. The maize MON 87419 event was produced by: (i) transformation of thousands of maize plant cells with a nucleic acid construct that includes the transgenes of interest, (ii) regeneration of a population of maize plants each containing a unique transgenic event, and (iii) multi-year testing, screening, and selection to select an event having the desirable agronomic properties, the maize MON 87419 event. The maize MON 87419 event is characterized by the unique DNA sequence of the insertion of the transgene into the particular location of the maize plant's genome.

The act of inserting the transgenic DNA into the genome of the maize plant is accomplished by the act of plant transformation and results in the creation of a new transgenic genomic molecular sequence, known as an "event". This sequence is unique to and specific for the event and can be readily identified when compared to the original maize genomic sequence or other transgenic maize events.

Molecular analysis of the maize MON 87419 event identified the genomic insertion site of the inserted DNA (SEQ ID NO:9) and the flanking maize genomic DNA sequence immediately adjacent to either side of the inserted DNA (SEQ ID NO:7 and SEQ ID NO:8). This arrangement of the inserted DNA in relation to the surrounding maize plant genome DNA is therefore specific and unique to the transgenic herbicide tolerant maize comprising the maize MON 87419 event. This new genomic molecular sequence (SEQ ID NO:10) is also an integral part of the chromosome of transgenic herbicide tolerant maize plants comprising the maize MON 87419 event and as such is static in the plant and may be passed on to progeny of the plant.

The present invention also provides progeny of the original transformant comprising the maize MON 87419 event. Such progeny may be produced by selfing of a maize plant comprising the maize MON 87419 event or by sexual outcross between a maize plant comprising the maize MON 87419 event and another plant that does or does not contain the maize MON 87419 event. Such other plant may be a transgenic plant comprising the same or different event(s) or a nontransgenic plant, such as one from a different variety. Even after repeated back-crossing to a recurrent parent, the maize MON 87419 event from the transformed parent is present in the progeny of the cross at the same genomic location.

As used herein, the term "maize" means *Zea mays* (also referred to as corn) and includes all plant varieties that can be bred with maize.

The invention provides a transgenic herbicide tolerant maize plant containing the maize MON 87419 event that is tolerant to dicamba (3,6-dichloro-2-methoxybenzoic acid) herbicide and glufosinate (2-amino-4-(hydroxymethylphosphinyl) butanoic acid) herbicide. Dicamba is a synthetic auxin herbicide useful for controlling broadleaf weeds. Glufosinate is an organophosporus herbicide useful for controlling a broad spectrum of annual and perennial grass and broadleaf weeds. The maize MON 87419 event contains a demethylase (dmo) gene from *Stenotrophomonas maltophilia* that expresses a dicamba mono-oxygenase (DMO) protein to confer tolerance to dicamba herbicide and a bialaphos resistance (pat) gene from *Streptomyces viridochromogenes* that expresses the phosphinothricin N-acetyltransferase (PAT) protein to confer tolerance to glufosinate herbicide.

As used herein, the term "recombinant" refers to a non-natural DNA, protein, or organism that would not normally be found in nature and was created by human intervention. As used herein, a "recombinant DNA molecule" is a DNA molecule comprising a combination of DNA molecules that would not naturally occur together and is the result of human intervention, for example, a DNA molecule that is comprised of a combination of at least two DNA molecules heterologous to each other, such as a DNA molecule that comprises a transgene and the plant genomic DNA adjacent to the transgene. An example of a recombinant DNA molecule is a DNA molecule comprising at least one sequence selected from SEQ ID NO:1-10. As used herein, a "recombinant plant" is a plant that would not normally exist in nature, is the result of human intervention, and contains a transgenic DNA molecule. As a result of such genomic alteration, the recombinant plant is something new and distinctly different from the related wild-type plant. An example of a recombinant plant is a maize plant containing the maize MON 87419 event.

As used herein, the term "transgene" refers to a DNA molecule artificially incorporated into an organism's genome as a result of human intervention, such as by plant transformation methods. A transgene may be heterologous to the organism. The term "transgene insert" as used herein refers to the transgene inserted by plant transformation techniques into the maize genome to produce maize event MON 87419. The sequence for this transgene insert is provided as SEQ ID NO:9. The term "transgenic" refers to comprising a transgene, for example a "transgenic plant" refers to a plant comprising a transgene.

As used herein, the term "heterologous" refers to a first molecule not normally associated with a second molecule or an organism in nature. For example, a DNA molecule may be derived from a first species and inserted into the genome of a second species. The DNA molecule would thus be heterologous to the genome and the organism.

As used herein, the term "chimeric" refers to a single DNA molecule produced by fusing a first DNA molecule to a second DNA molecule, where neither first nor second DNA molecule would normally be found in that configuration fused to the other. The chimeric DNA molecule is thus a new DNA molecule not normally found in nature. An example of a chimeric DNA molecule is a DNA molecule comprising at least one sequence selected from SEQ ID NO:1-10.

The invention provides DNA molecules and their corresponding DNA sequences. As used herein, the terms "DNA" and "DNA molecule" refer to a deoxyribonucleic acid (DNA) molecule. A DNA molecule may be of genomic or synthetic origin, and is by convention from the 5' (upstream) end to the 3' (downstream) end. As used herein, the term "DNA sequence" refers to the nucleotide sequence of a DNA molecule. The nomenclature used is that required by Title 37 of the United States Code of Federal Regulations § 1.822 and set forth in the tables in WIPO Standard ST.25 (1998), Appendix 2, Tables 1 and 3. By convention, the DNA sequences of the invention and fragments thereof are disclosed with reference to only one strand of the two complementary DNA sequence strands. By implication and intent, the complementary sequences of the sequences provided here (the sequences of the complementary strand), also referred to in the art as the reverse complementary sequences, are within the scope of the invention and are expressly intended to be within the scope of the subject matter claimed. Thus, as used herein references to SEQ ID NO:1-10 and SEQ ID NO:14-22 and fragments thereof include and refer to the sequence of the complementary strand and fragments thereof.

As used herein, the term "fragment" refers to a smaller piece of a whole. For example, fragments of SEQ ID NO:10 would include sequences that are at least about 20 consecutive nucleotides, at least about 25 consecutive nucleotides, at least about 30 consecutive nucleotides, at least about 35 consecutive nucleotides, at least about 40 consecutive nucleotides, at least about 45 consecutive nucleotides, at least about 50 consecutive nucleotides, at least about 60 consecutive nucleotides, at least about 70 consecutive nucleotides, at least about 80 consecutive nucleotides, at least about 90 consecutive nucleotides, or at least about 100 consecutive nucleotides of the complete sequence of SEQ ID NO:10.

The DNA sequence corresponding to the complete DNA sequence of the transgene insert and substantial segments of the maize genome DNA flanking either end of the transgene insert is provided as SEQ ID NO:10. The DNA sequences of the maize genomic DNA physically linked by phosphodiester bond linkage to and therefore flanking the 5' end of the transgene insert is provided as SEQ ID NO:1, SEQ ID NO:3, SEQ ID NO:5, and SEQ ID NO:7. The DNA sequence of the maize genomic DNA physically linked by phosphodiester bond linkage to and therefore flanking the 3' end of the transgene insert is provided as SEQ ID NO:2, SEQ ID NO:4, SEQ ID NO:6, and SEQ ID NO:8.

Transgenic maize containing the maize MON 87419 event comprises two regions referred to as junctions. A "junction" is where one end of the transgene insert has been connected to the genomic DNA. A junction spans or extends across a portion of the transgene insert and the adjacent flanking genomic DNA and as such is the connection point of these two as one contiguous molecule. One junction is at the 5' end of the transgene insert and one is at the 3' end of the transgene insert, referred to herein as the 5' and 3' junction, respectively. A "junction sequence" refers to a DNA sequence of any length that spans the 5' or 3' junction of an event. Junction sequences of the maize MON 87419 event are readily apparent to one of skill in the art using SEQ ID NO:10. Examples of junction sequences of the maize MON 87419 event are provided as SEQ ID NO:1-8. FIG. 1 illustrates the physical arrangement of SEQ ID NO:1-10 arranged from 5' to 3'. The invention thus provides a DNA molecule that contains at least one of the DNA sequences as set forth in SEQ ID NO:1-8.

The junction sequences of the maize MON 87419 event may be present as part of the genome of a transgenic maize plant, seed, or cell containing the maize MON 87419 event. The identification of any one or more of SEQ ID NO:1-8 in a sample derived from a transgenic maize plant, plant part, seed, or cell indicates that the DNA was obtained from transgenic maize containing the maize MON 87419 event and is diagnostic for the presence of the maize MON 87419 event.

The maize MON 87419 event contains sequences which are unique to the transgene insert, specifically SEQ ID NO:14-22. These sequences are unique to the specific chimeric configuration of the various promoters, introns, chloroplast targeting peptides (CTP), 3' termination signal, the pat and dmo genes within the transgene insert of the event. FIG. 1 illustrates the relative position of each of these unique transgene insert sequences with respect to SEQ ID NO:9.

Provided are exemplary DNA molecules that can be used either as primers or probes for diagnosing the presence in a sample of DNA derived from the maize MON 87419 event. Such primers or probes are specific for a target nucleic acid sequence and as such are useful for the identification of the maize MON 87419 event by the methods described here.

A "primer" is a DNA molecule that is designed for use in annealing or hybridization methods that involve an amplification reaction. An amplification reaction is an in vitro reaction that amplifies template DNA to produce an amplicon. As used herein, an "amplicon" is a DNA molecule that has been synthesized using amplification techniques. Amplicons of the invention have a DNA sequence comprising one or more of SEQ ID NO:1-10, or fragments thereof. A pair of primers may be used with template DNA, such as a sample of maize genomic DNA, in an amplification reaction, such as polymerase chain reaction (PCR), to produce an amplicon, where the amplicon produced would have a DNA sequence corresponding to sequence of the template DNA located between the two sites where the primers hybridized to the template. A primer is typically designed to hybridize to a complementary target DNA strand to form a hybrid between the primer and the target DNA strand. The presence of a primer is a point of recognition by a polymerase to begin extension of the primer using as a template the target DNA strand. Primer pairs refer to use of two primers binding opposite strands of a double stranded nucleotide segment for the purpose of amplifying the nucleotide segment between them. Examples of primer sequences are provided as SEQ ID NO:11 and SEQ ID NO:12. The primer pair provided as SEQ ID NO:11 and SEQ ID NO:12 are useful as a first DNA molecule and a second DNA molecule, where the first DNA molecule is a fragment of SEQ ID NO:9 and the second DNA molecule is a fragment of the maize genomic DNA sequence of SEQ ID NO:10, and each are of sufficient length to function as DNA primers when used together in an amplification reaction with DNA containing the maize MON 87419 event to produce an amplicon diagnostic for the maize MON 87419 event in a sample. The maize genomic DNA sequence of the maize MON 87419 event is provide as positions 1-1246 and 8009-9259 of SEQ ID NO:10.

A "probe" is a nucleic acid molecule that is complementary to a strand of a target nucleic acid and useful in hybridization detection methods. Probes according to the invention include not only deoxyribonucleic or ribonucleic acids but also polyamides and other probe materials that bind specifically to a target DNA sequence and the detection of such binding can be useful in detecting the presence or absence of the target DNA sequence. A probe may be attached to a conventional detectable label or reporter molecule, such as a radioactive isotope, ligand, chemiluminescent agent, or enzyme. An exemplary DNA sequence useful as a probe for detecting maize MON 87419 event is provided as SEQ ID NO:13.

Methods for designing and using primers and probes are well known in the art, and DNA molecules comprising fragments of SEQ ID NO:1-10 and useful as primers and probes for detecting the maize MON 87419 event can readily be designed by one of skill in the art.

The DNA molecules and corresponding DNA sequences provided herein are therefore useful for identifying the maize MON 87419 event in transgenic maize plants, cells, seeds, or parts; selecting maize varieties or hybrids comprising the maize MON 87419 event; and detecting the presence or absence of the maize MON 87419 event in a sample.

As used herein, the term "isolated" refers to separating a molecule from other molecules normally associated with it in its native or natural state. The term "isolated" thus may refer to a DNA molecule that has been separated from other DNA molecule(s) which normally are associated with it in its native or natural state. Such a DNA molecule may be present in a recombined state, such as a recombinant DNA molecule. Thus, DNA molecules fused to regulatory or coding sequences with which they are not normally associated, for example as the result of recombinant techniques, are considered isolated, even when integrated as a transgene into the chromosome of a cell or present with other DNA molecules.

The invention provides maize plants, progeny, seeds, plant cells, and plant parts containing the maize MON 87419 event, and commodity products produced using these. A representative sample of transgenic herbicide tolerant maize seed comprising MON 87419 event has been deposited according to the Budapest Treaty with the American Type Culture Collection (ATCC®). The ATCC repository has assigned the Patent Deposit Designation PTA-120860 to the seed of the transgenic herbicide tolerant maize plant containing the maize MON 87419 event. The plants, progeny, seeds, plant cells, plant parts, and commodity products of the invention contain a detectable amount of DNA having at least one of the sequences provided as SEQ ID NO:1-10 and SEQ ID NO:14-22. Plants, progeny, seeds, plant cells, and plant parts of the invention may also contain one or more additional transgenic traits, particularly those introduced by crossing a maize plant containing the maize MON 87419 event with another plant containing the additional transgenic trait(s). Such traits include but are not limited to increased insect resistance, increased water use efficiency, increased yield performance, increased drought resistance, increased seed quality, improved nutritional quality, hybrid seed production, and/or increased herbicide tolerance, in which the trait is measured with respect to a maize plant lacking such transgenic trait.

Plants of the invention may be used to produce progeny that contain the maize MON 87419 event. As used herein, "progeny" includes any plant, seed, and plant cell comprising the maize MON 87419 event inherited from an ancestor plant, indicated by the plant comprising a DNA molecule having at least one sequence selected from SEQ ID NO:1-10. Plants, progeny, and seeds may be homozygous or heterozygous for the maize MON 87419 event. Progeny plants may be grown from seeds produced by a maize plant containing the maize MON 87419 event or from seeds produced by a maize plant fertilized with pollen containing the maize MON 87419 event.

As used herein, a "plant part" of the invention is any part derived from a transgenic maize plant containing the maize MON 87419 event. Plant parts include but are not limited to pollen, ovule, pod, flower, roots, stems, fibers, and leaves. Plant parts may be viable or nonviable.

The invention provides a commodity product that is produced from transgenic maize containing the maize MON 87419 event. Commodity products of the invention contain a detectable amount of DNA comprising a DNA sequence selected from the group consisting of SEQ ID NO:1-10. As used herein, a "commodity product" refers to any composition or product which is comprised of material derived from a transgenic maize plant, maize seed, maize plant cell, or maize plant part containing the maize MON 87419 event. Commodity products include but are not limited to processed seeds, grains, plant parts, and meal. Transgenic maize containing the maize MON 87419 event can be used to manufacture any commodity product typically acquired from maize. A commodity product of the invention will contain a detectable amount of DNA corresponding to the maize MON 87419 event. Detection of one or more of this DNA in a sample may be used for determining the content or the source of the commodity product. Any standard method of detection for DNA molecules may be used, including methods of detection disclosed herein.

The invention provides methods for controlling weeds using glufosinate or dicamba, or glufosinate and dicamba herbicides with transgenic maize containing the maize MON 87419 event. A method for controlling weeds in an area, such as a field, is provided that consists of planting transgenic maize plants containing the maize MON 87419 event in an area and applying an herbicidally effective dose of glufosinate or dicamba, or glufosinate and dicamba herbicides to the area for the purpose of controlling weeds in the area without injuring the transgenic maize plants containing the maize MON 87419 event. Such application of glufosinate or dicamba, or glufosinate and dicamba herbicides may be pre-emergence (any time after transgenic maize seed containing the maize MON 87419 event is planted and before transgenic maize plants containing the maize MON 87419 event emerge) or post-emergence (any time after transgenic maize plants containing the maize MON 87419 event emerge). A herbicidally effective dose of glufosinate for use in the area for controlling weeds should consist of a range from about 0.1 pound acid equivalent per acre (ae/ac) to as much as about 16 pounds ae/ac of glufosinate over a growing season. A herbicidally effective dose of dicamba for use in the area for controlling weeds should consist of a range from about 0.1 pound ae/ac to as much as about 16 pounds ae/ac of dicamba over a growing season. Multiple applications of glufosinate or dicamba, or glufosinate and dicamba herbicides may be used over a growing season, for example, two applications (such as a pre-planting application and a post-emergence application or a pre-emergence application and a post-emergence application) or three applications (such as a pre-planting application, a pre-emergence application, and a post-emergence application).

As used herein, the "active ingredient" or "ai" is the component of an herbicide formulation responsible for the herbicidal activity, often measured in pounds per gallon or applied as pounds per acre. For herbicides that are acids (for example, molecules that have a carboxyl group as part of their structure), the acidic group is often converted to (may be replaced by the desired ions to form) a salt or (reacted with an alcohol to form) an ester during the formulation process. This may alter not only the chemical characteristics of a particular herbicide molecule, but also the mass. However, the corresponding acid is the herbicidally active portion of the formulation and equivalency of herbicidal activity between different active ingredients can be calculated using the acid equivalent as the standard unit of measurement. The term "acid equivalent" or "ae" means the portion of an active ingredient in a formulation that theoretically could be converted back to the corresponding acid. Herbicide application rates may be expressed as "acid equivalent per acre" (abbreviated as "ae/ac") or as "active ingredient per acre" (abbreviated as "ai/ac").

Methods for producing an herbicide tolerant transgenic maize plant containing the maize MON 87419 event are provided. Progeny produced by these methods may be varietal or hybrid plants; may be grown from seeds produced by a transgenic maize plant containing the maize MON 87419 event or from seeds produced by a maize plant fertilized with pollen from a transgenic maize plant containing the maize MON 87419 event; and may be homozygous or heterozygous for the maize MON 87419 event. Plants may be self-pollinated (also known as "selfing") or cross-pollinated (also known as "crossing"). Transgenic maize plants containing the maize MON 87419 event may be self-pollinated to generate a true breeding line of plants that are homozygous for the maize MON 87419 event. Selfing results in progeny known as "inbred" and is used to produce inbred lines that are genetically uniform. Alternatively, transgenic maize plants containing the maize MON 87419 event may be outcrossed (bred with another plant that is transgenic or nontransgenic) to produce a varietal or a hybrid seed. Seed and progeny plants made by the methods of the invention would contain the maize MON 87419 event and may then be treated with glufosinate or dicamba, or glufosinate and dicamba herbicides. Treatment with glufosinate or dicamba, or glufosinate and dicamba herbicides may be used to select progeny that are tolerant. Alternatively, these progeny plants may be analyzed using diagnostic methods to select for plants or seeds containing the maize MON 87419 event.

Plants, progeny, seeds, plant cells, and plant parts of the invention may also contain one or more additional maize transgenic traits, particularly those introduced by crossing a maize plant containing the maize MON 87419 event with another maize plant containing the additional transgenic trait(s). Such maize transgenic traits include, but are not limited to, increased insect resistance, increased water use efficiency, increased yield performance, increased drought resistance, increased seed quality, improved nutritional quality, hybrid seed production, and herbicide tolerance, in which the trait is measured with respect to a maize plant lacking such transgenic trait. Such maize transgenic traits are known to one of skill in the art; for example, a list of such traits is provided the United States Department of Agriculture's (USDA) Animal and Plant Health Inspection Service (APHIS) and can be found on their website at http://www.aphis.usda.gov. Two transgenic plants may thus be crossed to produce progeny that contain two or more independently segregating transgenic traits. Back-crossing to a parental plant and out-crossing with a non-transgenic plant are also contemplated, as is vegetative propagation. Descriptions of breeding methods that are commonly used for different traits and crops can be found in one of several references, for example, Fehr, in Breeding Methods for Cultivar Development, Wilcox J. ed., American Society of Agronomy, Madison Wis. (1987).

The plants, seeds, cells, plant parts, and commodity products of the invention may be used for detection of DNA and protein molecules indicative of the presence of the maize MON 87419 event. Such detection would be done using the DNA sequences provided herein and the respective DMO and PAT protein sequences encoded by the transgene insert that is provided as SEQ ID NO:9. Detection of the presence of the maize MON 87419 event may be done by using methods known in the art, such as thermal amplification of nucleic acid, nucleic acid hybridization techniques (such as northern blotting and southern analysis), protein detection techniques (such as western blotting, immunoprecipitation, and enzyme-linked immunosorbent assay-based (ELISA) techniques) or by using the methods of detection and/or the detection kits provided herein. One method provides for contacting a DNA sample with a primer pair that is capable of producing an amplicon from DNA of the transgenic maize containing the maize MON 87419 event, performing an amplification reaction and thereby producing a DNA amplicon comprising at least one of the DNA sequences provided as SEQ ID NO:1-10 and SEQ ID NO:14-22, and then detecting the presence or absence of the amplicon molecule and optionally confirming within the sequence of the amplicon a sequence comprising at least one of the sequences provided as SEQ ID NO:1-10 and SEQ ID NO:14-22. The presence of such an amplicon is diagnostic for the presence of DNA specific for the transgenic maize containing the maize MON 87419 event and thus biological material in the sample that is derived from transgenic maize containing the maize MON 87419 event. Another method provides for contacting a DNA sample with a DNA probe, subjecting the probe and the DNA sample to stringent hybridization conditions, and then detecting hybridization between the probe and the target DNA sample. Detection of hybridization is diagnostic for the presence of DNA specific for the transgenic maize containing the maize MON 87419 event in the DNA sample.

DNA detection kits for the maize MON 87419 event are provided. Variations on such kits can also be developed using the compositions and methods disclosed herein and the methods well known in the art of DNA detection. DNA detection kits can be applied to methods for breeding with transgenic maize plants containing the maize MON 87419 event. Such kits contain DNA primers or probes comprising fragments of SEQ ID NO:1-10. One example of such a kit comprises at least one DNA molecule of sufficient length of contiguous nucleotides of SEQ ID NO:10 to function as a DNA probe useful for detecting the presence and/or absence in a sample of DNA derived from transgenic herbicide tolerant maize plants containing the maize MON 87419 event. A DNA molecule sufficient for use as a DNA probe is provided that is useful for determining, detecting, or diagnosing the presence and/or absence in a sample of transgenic herbicide tolerant maize containing the maize MON 87419 event DNA is provided as SEQ ID NO:13. Other probes may be readily designed by one of skill in the art and should comprise at least about fifteen nucleotides of SEQ ID NO:10 and be sufficiently unique to transgenic herbicide tolerant maize containing the maize MON 87419 event DNA in order to identify DNA derived from the maize MON 87419 event. Another type of kit comprises a primer pair useful for producing an amplicon useful for detecting the presence or absence in a sample of the maize MON 87419 event. Such a kit would employ a method comprising contacting a target DNA sample with a primer pair, then performing a nucleic acid amplification reaction sufficient to produce an amplicon comprising a DNA molecule having at least one sequence selected from SEQ ID NO:1-10, and then detecting the presence or absence of the amplicon. Such a method may also include sequencing the amplicon or a fragment thereof. Other primer pairs may be readily designed by one of skill in the art and should comprise at least twenty nucleotides of SEQ ID NO:10 and be sufficiently unique to the transgenic herbicide tolerant maize containing the maize MON 87419 event DNA in order to detect the maize MON 87419 event. Kits of the invention may optionally also comprise reagents for performing the detection or diagnostic reactions described herein or instructions for the use of the kit and its contents.

As used herein, the term "comprising" means "including but not limited to".

Deposit Information

A deposit of a representative sample of transgenic maize seed comprising the maize MON 87419 event has been made according to the Budapest Treaty with the American Type Culture Collection (ATCC) having an address at 10801 University Boulevard, Manassas, Va. USA, Zip Code 20110. The ATCC Patent Deposit Designation (accession number) for seeds comprising the maize MON 87419 event is PTA-120860 and the date of deposit was Jan. 17, 2014. The deposit will be maintained in the depository for a period of 30 years, or 5 years after the last request, or for the effective life of the patent, whichever is longer.

EXAMPLES

The following examples are included to more fully describe the invention. It should be appreciated by those of skill in the art that many modifications can be made in the specific examples which are disclosed and still obtain a similar result. Certain agents which are both chemically and physiologically related may be substituted for the agents described herein while achieving the same or similar results. All such substitutions and modifications apparent to those skilled in the art are deemed to be within the scope of the invention.

Example 1: MON 87419 Event Production and Selection

This example describes the production, analysis, and selection of transgenic maize containing the event MON 87419, an event which can provide tolerance to both dicamba and glufosinate herbicides. Summarized are the production and analysis of tens of thousands of individual plants over multiple years through the rigorous molecular, phenotypic, and field testing required for the ultimate selection of the maize MON 87419 event.

Transformation vectors containing a variety of different expression cassettes were designed and tested to confirm their utility for expressing the dmo and pat genes. Using this data, expression element combinations were selected and eight different transformation vectors were constructed and transformed into maize. These vectors tested promoters and terminators in various combinations with the two coding regions for the pat gene and the dmo gene (Table 1). The resulting plants were analyzed for protein expression and two vectors (shown as A and B in Table 1) were selected for commercial maize transformation.

TABLE 1

Cassette Configuration of Transformation Vectors.

| | cassette 1 (PAT) | | | cassette 2 (DMO) | | |
|---|---|---|---|---|---|---|
| Vector | Promoter | Gene of Interest | Terminator | Promoter | Gene of Interest | Terminator |
| A | AND.ge.Ubq1 | PAT | Os.Ara5 | PCSV/I-Act1 | CTP4/DMO | Hsp17.5 |
| B | P-1 | PAT | T-1 | PCSV/I-Act1 | CTP4/DMO | Hsp17.5 |
| C | AND.ge.Ubq1 | PAT | Os.Ara5 | P-1 | CTP4/DMO | Hsp17.5 |
| D | P-1 | PAT | T-1 | AND.ge.Ubq1 | CTP4/DMO | Hsp17.5 |
| E | AND.ge.Ubq1 | PAT | Os.Ara5 | P-2 | CTP4/DMO | Hsp17.5 |
| F | AND.ge.Ubq1 | PAT | Os.Ara5 | P-3 | CTP4/DMO | Hsp17.5 |
| G | P-1 | PAT | T-1 | P-2 | CTP4/DMO | Hsp17.5 |
| H | P-1 | PAT | T-1 | P-3 | CTP4/DMO | Hsp17.5 |

Over thirteen thousand unique transformed maize plants were produced using the two vectors (A and B) that were selected. In plants there is often wide variation in the levels of expression of an introduced gene among individual events, and gene expression can directly correlate positively or negatively with the phenotype of the plant containing the event. The expression of foreign genes in plants is known to be influenced, among other things, by their chromosomal position. For this reason, it was necessary to screen a large number of individual plants containing random insertion events through multiple years and locations to identify the optimal event. The transgenic maize MON 87419 event was created through *Agrobacterium*-mediated transformation of LH244 maize immature embryos. Methods for transforming maize are known in the art. Maize cells were transformed and regenerated into intact maize plants. Rooted plants with normal phenotypic characteristics were selected. Thousands of individual, independent events were then transferred to soil for growth and further assessment.

TABLE 2

Event Selection Process

| Milestone | | Vector A Events Advanced | Vector B Events Advanced | Total Unique Events Advanced |
|---|---|---|---|---|
| R0 Evaluation | Transgenic Events Produced | 5236 | 8413 | 13649 |
| | First Pass Single Copy analysis | 1300 | 1698 | 2998 |
| | R0 Spray | 642 | 798 | 1440 |
| | Initial Detailed Molecular Analysis | 85 | 99 | 184 |
| | R0 Southern | 54 | 58 | 112 |
| Early Screens (R1 & R2) | R1 Trials & molecular analysis | 22 | 22 | 44 |
| | R2 Trials & molecular analysis | 20 | 22 | 42 |
| Advanced Field Trials & Molecular Analysis | SA Year 1 | 7 | 10 | 17 |
| | US Year 1 | 5 | 6 | 11 |
| | SA Year 2 | 2 | 3 | 5 |
| | In-depth evaluation | 2 | 0 | 2 |
| | Final event selection | 1 | 0 | 1 |

Throughout the event selection process, molecular analysis as well as field trials to assess phenotype, agronomics, and efficacy of the events were conducted, often concurrently (Table 2). The 13,000 individual, unique transformed maize R0 plants were analyzed first by PCR to select for events with a single copy of the transgene insert (First Pass Single Copy). This resulted in the advancement of 2,998 events. The next selection was R0 herbicide spray tolerance conducted in a green house. The plants were tested for tolerance to both glufosinate (Ignite® 280 herbicide) and dicamba (Clarity® herbicide) by using a tank mix of glufosinate (0.9 lb ai/ac) and dicamba (2.0 lb ae/ac) sprayed at the V1/V2 growth stage. Plants that showed >15% injury were discarded, and 1,440 events were selected for further analysis. An initial detailed molecular analysis was conducted and included sequence identification and confirmation, and a second check of copy number and absence of backbone. This analysis resulted in 184 events containing only a single copy of the transgene insert selected for advancement. Southern analysis on DNA extracted from R0 events was done to further confirm transgene insert copy number and to confirm absence of transformation backbone. Based on this, 112 events were selected for advancement to R1 for further analysis. R0 plants were self-pollinated and seed was collected for R1 trials.

Concurrently with all field trials, additional molecular analysis was in progress. Northern analysis was done to detect and measure mRNA transcripts of the pat and dmo genes. N-terminal protein sequencing of the PAT and DMO proteins purified from transgenic plants containing select events was done to confirm the recombinant protein sequence. Western analysis to detect the PAT and DMO proteins was done with transgenic plant samples. Sequencing of the entire transgene and both the 5' and 3' ends of the insert was conducted and subsequently used to develop methods of detecting individual events. In depth Southern analysis was performed on R1 plants to confirm copy number and the absence of backbone.

For the R1 field trial early screens, of the 112 events selected from the R0 screening 82 events were selected based on seed return and nursery size considerations. The R1 plants were segregating, and thus were null, hemizygous, or homozygous for an event. The 82 events in R1 plants were evaluated in a field efficacy screen with high rates of herbicide application. Plant injury was assessed following treatments with various combinations of glufosinate (Ignite 280) and dicamba (Clarity) (up to 20× glufosinate and up to 16× dicamba labeled field application rates) and with application timing at various growth stages from V1/V2 to V8/V10. Injury ratings were taken 10 to 14 days after herbicide application. Standard injury ratings include scoring for percent chlorosis, malformation, and breeding. Overall averages for multiple plants containing the same event were used to select events for advancement. Herbicide applications at 2× rates generally produced less than 10% injury, and herbicide application at the 16× and 20× rates produced injury ratings of more than 10%. In addition to the efficacy testing, agronomic scoring was collected for each plant and correlated to the event it contained. The agronomic scoring criteria that were evaluated included plant height, ear height, percent moisture, test weight, days to 50% pollen, and days to 50% silk. Based on analysis of the data collected from the R1 field trials and the molecular analysis, 44 events were selected for advancement to R2 for further analysis. R1 plants were self-pollinated and seed was collected for R2 trials.

In the R2 field trial early screens, R2 and F1 events (from an R1 outcross) were evaluated in field efficacy screens at three locations (two states and Puerto Rico). Plant injury was assessed following treatments with various combinations of glufosinate and dicamba application rates and application timing. The R2 plants are homozygous for the event, and the herbicide tolerance failure rate after herbicide application was low, confirming the R1 results. Agronomic data was collected and scored as in the R1 field trials. Additional molecular analysis, including gene expression analysis, was also used to select plants containing the best events. Based on analysis of the data collected from the R2 and F1 field trials and the molecular analysis, 42 events were selected for advancement to R3 for further analysis. R2 plants were self-pollinated and seed was collected for R3 trials.

For the advanced field trials, both hybrid and inbred efficacy and hybrid and inbred agronomic field trials were conducted. The agronomic field trials were run during the same season as the efficacy field trials. All field trials used a randomized complete block design and were conducted at multiple locations. For both efficacy and agronomic field trials, agronomic scoring was collected throughout the field trial season, and at the end of the season yield was determined (efficacy yield or agronomic yield). Efficacy field trials were conducted to assess crop injury 10 to 14 days following herbicide application, crop injury ratings, and yield. The target crop injury rating was a score of less than 10% for advancement of the event. For agronomic field trials, the plots were maintained weed free and no glufosinate or dicamba herbicide was applied during the growing season. The hybrid agronomic field trials included controls of a comparable hybrid (hybrid control) produced using the same parental maize lines used to make the transgenic hybrid cross, but not containing a transgenic event. Inbred controls were a comparable inbred to the transgenic inbred lines.

A meta-analysis was performed using the aggregate of the multi-season, multi-location field trial data. Table 3 illustrates the number of replications for which an observation was repeated for the particular field trial type for plants containing either one of the events. For each of the two events, there were 135 data points recorded for hybrid agronomic performance, 933 data points for hybrid efficacy, 179 data points for inbred agronomics, 30 data points for inbred efficacy, and 16 data points for event based pressure testing of herbicide application rates for maize containing the event.

TABLE 3

Field trial replications for two final events.

| Description | Reps per event |
| --- | --- |
| Hybrid Agronomics | 135 reps |
| Hybrid Efficacy | 933 reps |
| Inbred Agronomics | 179 reps |
| Inbred Efficacy | 30 reps |
| Event based Pressure Test | 16 reps |
| Total Replications per event | 1293 |

Hybrid plants each containing one of 23 selected events (a subset of the 42 events from the R2 field trial) were evaluated in South America (SA) Year 1 contra-season efficacy field trials and agronomic field trials. Trials were conducted at six locations in a randomized complete block design with 4 treatments and 2 replications per treatment. In the efficacy field trials, the dicamba formulation was Banvel® 4SL herbicide and the glufosinate formulation was Liberty® 1.67SL. Herbicide treatments consisted of the following: (1) non-treated control; (2) dicamba at 2 lbs ae/acre (ac) PRE (where PRE is defined as at planting or before crop emergence) followed by dicamba at 1 lb ae/ac applied at each of VE-V2 followed by V4 followed by V8; (3) glufosinate applied at 0.8 lb ai/ac at VE-V2 followed by V4 followed by V8; and (4) glufosinate applied at 0.8 lb ai/ac plus dicamba applied at 1 lb ae/ac at VE-V2 followed by V4 followed by V8. Injury ratings were taken at 10 to 14 days after herbicide application. Overall averages for multiple plants containing the same event were used to select events for advancement. The target crop injury rating was a score of less than 10%, and the observed injury rating was below 1%. Based upon hybrid injury scoring, agronomic scoring, efficacy yield, agronomic yield, and additional molecular analysis, 17 events were selected for advancement.

Inbred and hybrid plants from the 17 events advanced from the SA Year 1 contra-season field trials were then further evaluated in United States (US) Year 1 efficacy field trials and agronomic field trials. These trials were conducted in 2012, which was a season of severe drought in the United States. The hybrid efficacy field trials were conducted at 12 locations, 2 states in a randomized complete block design with 6 treatments and 3 replications per treatment. The hybrid plants containing the transgenic event derived glyphosate tolerance from the male parent in the cross. In these efficacy field trials, the glyphosate formulation was Roundup PowerMAX® 4.5SL, the dicamba formulation was Clarity 4SL, and the glufosinate formulation was Ignite 280 2.34SL. Herbicide treatments consisted of the following: (1) non-treated control; (2) glyphosate at 3 lbs ae/ac applied at V4 followed by V8; (3) glufosinate at 0.8 lb ai/ac applied at V2 followed by V4 followed by V8; (4) dicamba at 2 lbs ae/ac applied PRE and then again applied at V4 followed by V8; (5) glyphosate at 3 lbs ae/ac plus dicamba at 1.5 lbs ae/ac applied at V2 followed by V4 followed by V8; (6) dicamba at 2 lbs ae/ac applied at V2 followed by glufosinate at 0.8 lbs ai/ac plus dicamba at 1 lb ae/ac applied at growth stage V4 followed by glyphosate at 3 lbs ae/ac plus dicamba at 1.5 lbs ae/ac applied at growth stage V8. Injury ratings were taken 10 to 14 days after herbicide application. Overall averages for multiple plants containing the same event were used to select events for advancement. The target crop injury rating was a score of less than 10%, and the observed injury rating was below 1%. Based on hybrid injury scoring, agronomic scoring, efficacy yield, agronomic yield, and additional molecular analysis, 11 events were selected for advancement.

South America (SA) Year 2 contra-season field trials to assess hybrid efficacy and inbred agronomic yield were then conducted with plants containing these 11 events. The hybrid plants containing the transgenic event derived glyphosate tolerance from the male parent in the cross. The hybrid efficacy field trials were conducted essentially as described for South America (SA) year 1 contra-season field trials but with the following herbicide treatments: (1) non-treated control; (2) glyphosate at 3 lbs ae/ac applied at V4 followed by V8; (3) glufosinate at 0.8 lb ai/ac applied at V4 followed by V8; (4) dicamba at 2 lbs ae/ac applied PRE and then again applied at V4 followed by V8; (5) glyphosate at 3 lbs ae/ac plus dicamba at 1.5 lbs ae/ac applied at V4 followed by V8; (6) glufosinate at 0.8 lbs ai/ac plus dicamba at 1 lb ae/ac applied at V4 followed by glyphosate at 3 lbs ae/ac plus dicamba at 1.5 lbs ae/ac applied at V8. Injury ratings were taken 10 to 14 days after herbicide application. Overall averages for multiple plants containing the same event were used to select events for advancement. Based on hybrid injury scoring, agronomic scoring, hybrid efficacy yield, inbred agronomic yield, and additional molecular analysis, 5 events were selected for advancement.

Additional molecular analysis was then completed for these 5 events. The multi-year field and molecular data for each of the 5 events, including hybrid trait efficacy field trials, hybrid and inbred yield measurements, agronomic scoring, and molecular information was then reviewed, and two events were selected for further analysis. Both of these events were produced using the same transformation vector, and therefore had the same transgene insert but not the same genomic location or flanking sequence.

United States (US) Year 2 hybrid and inbred efficacy field trials, and hybrid and inbred agronomic field trials were conducted to evaluate these two events. The hybrid efficacy trials were done similar to year 1 US field trials, but included different spray regimens. Efficacy was measured by injury ratings and hybrid efficacy yield. Additional molecular analysis for the events was also done. The hybrid plants containing the transgenic event derived glyphosate tolerance from the male parent in the cross. The hybrid Efficacy 1 and 2 field trials were conducted at twelve locations across two states and the hybrid Efficacy 3 field trials were conducted at thirty-three locations across four states. In these field trials, the glyphosate formulation was Roundup PowerMAX 4.5SL, the dicamba formulation was Clarity 4SL, and the glufosinate formulation was Ignite 280 2.34SL. Herbicide applications for the Efficacy 1 and Efficacy 2 trials (with crosses to two separate inbred lines) were: (1) non-treated control; (2) glufosinate at 0.4 lb ai/ac applied at VE-V2 followed by V6; (3) glufosinate at 0.8 lb ai/ac applied at VE-V2 followed by V6; (4) dicamba at 0.5 lbs ae/ac applied at V4 followed by V8; (5) dicamba at 1.0 lbs ae/ac applied at V4 followed by V8; and (6) glyphosate at 2.25 lbs ae/ac plus dicamba at 1.0 lbs ae/ac applied at V4 followed by V8. Herbicide applications for the Efficacy 3 trial (representing hybrid from a cross with a third inbred line) were: (1) non-treated control; (2) dicamba at 0.5 lbs ae/ac applied at VE-V2 followed by glufosinate at 0.4 lb ai/ac applied at V6; and (3) dicamba at 1.0 lbs ae/ac applied at VE-V2 followed by glufosinate at 0.8 lb ai/ac applied at V6. Injury ratings were taken 10 to 14 days after herbicide application and for multiple plants containing the same event were used to select events for advancements. Yield and agronomic data was collected.

To compare the hybrid injury ratings for the two events, meta-analysis of the multiple hybrid efficacy field trials was completed. (Table 4) Injury rating was scored at V8 (where V8 analysis encompasses the cumulative injury from V2, V4, V6, and V8 herbicide applications) with a statistical least significant difference (LSD at $p<0.05$). Tester 1, Tester 2, and Tester 3 represent crosses with 3 independent inbred maize parent lines, which were used to generate the hybrid for the indicated field trial. For each of the trials, no statistical difference in injury rating was found between hybrids generated using a transgenic maize parent containing either of the two events.

TABLE 4

Meta-analysis of injury rating from hybrid efficacy field trials.

| Field Trial | Transgenic Maize | V8 injury | LSD (P < 0.05) |
|---|---|---|---|
| Year 1 combined SA and US | MON 87419 | 0.43 | 0.3 |
| Year 1 combined SA and US | EVENT 2 | 0.49 | 0.3 |
| SA Year 2 Hybrid Efficacy | MON 87419 | 2.58 | 3 |
| SA Year 2 Hybrid Efficacy | EVENT 2 | 1.98 | 3 |
| US Year 2 Hybrid Tester 1 | MON 87419 | 0 | 0 |
| US Year 2 Hybrid Tester 1 | EVENT 2 | 0 | 0 |
| US Year 2 Hybrid Tester 2 | MON 87419 | 0 | 0 |
| US Year 2 Hybrid Tester 2 | EVENT 2 | 0 | 0 |
| US Year 2 Hybrid Tester 3 | MON 87419 | 0.31 | 0.42 |
| US Year 2 Hybrid Tester 3 | EVENT 2 | 0.12 | 0.42 |

A meta-analysis of the hybrid efficacy yield (bushels/acre) from the multiple efficacy field trials was completed comparing yield from hybrids containing each of the two events. (Table 5) For each of the trials, no statistical difference in hybrid efficacy yield was found between hybrids generated using a transgenic maize parent containing either of the two events.

TABLE 5

Meta-analysis of yield from hybrid efficacy field trials.

| Field Trial | Hybrid Maize | Yield (Bu/ac) | LSD (p < 0.05) |
|---|---|---|---|
| Year 1 combined SA and US | MON 87419 | 171.07 | 4 |

TABLE 5-continued

Meta-analysis of yield from hybrid efficacy field trials.

| Field Trial | Hybrid Maize | Yield (Bu/ac) | LSD (p < 0.05) |
|---|---|---|---|
| Year 1 combined SA and US | EVENT 2 | 172.90 | 4 |
| SA Year 2 | MON 87419 | 233.66 | 14 |
| SA Year 2 | EVENT 2 | 231.59 | 14 |
| US Year 2 Tester 1 | MON 87419 | 217.43 | 10 |
| US Year 2 Tester 1 | EVENT 2 | 220.06 | 10 |
| US Year 2 Tester 2 | MON 87419 | 219.68 | 7 |
| US Year 2 Tester 2 | EVENT 2 | 221.21 | 7 |
| US Year 2 Tester 3 | MON 87419 | 208.76 | 5.67 |
| US Year 2 Tester 3 | EVENT 2 | 213.02 | 5.67 |

Pressure testing field trials were also conducted with hybrid transgenic maize containing either one of the two events. In the pressure tests, either glufosinate (Ignite 280, 2.34SL) or dicamba (Clarity 4SL) herbicide was applied at non-commercially high rates. For typical field trials, the 1× rate for glufosinate was 0.4 lb ai/ac and the 1× rate for dicamba was 0.5 lb ae/ac. For the glufosinate pressure testing field trials, glufosinate was applied at VE-V2 followed by V4 followed by V8 at the following rates: (1) 1 lb ai/ac (2.5×); (2) 2 lb ai/ac (5×); (3) 4 lb ai/ac (10×); and (4) 8 lb ai/ac (20×). For the dicamba pressure testing field trials, dicamba was applied at VE-V2 followed by V4 followed by V8 at the following rates: (1) 2 lb ae/ac (4×); (2) 4 lb ae/ac (8×); (3) 8 lb ae/ac (16×); and (4) 16 lb ae/ac (32×). At the end of the season, the hybrid pressure testing field trials were harvested and yield (bushels/acre or bu/ac) was determined. An analysis of the yield data compared hybrids containing either of the two events. For each of the trials, no statistical difference in yield at any of the herbicide application rates was found between hybrids generated using a transgenic maize parent containing either of the two events.

TABLE 6

Yield from hybrid pressure testing efficacy field trials.

| Field Trial | Transgenic Hybrid Maize | Yield (Bu/ac) | LSD (p < 0.05) |
|---|---|---|---|
| Glufosinate Pressure Test 2.5-20X | MON 87419 | 207.31 | 40 |
| Glufosinate Pressure Test 2.5-20X | EVENT 2 | 201.65 | 40 |
| Dicamba Pressure Test 4-32X | MON 87419 | 239.93 | 40 |
| Dicamba Pressure Test 4-32X | EVENT 2 | 234.60 | 40 |

Hybrid agronomic field trials were conducted in 3 sets with 15 locations per set at 21 locations across 3 states and were run during the same season with the hybrid efficacy field trials. Agronomic measures were collected through out the field trial season, and at the end of the season agronomic yield was determined. Meta-analysis across the multi-season, multi-location hybrid agronomic field trials was used to compare the yield of the hybrid control and the hybrids containing the either one of the two events. No statistical difference in hybrid agronomic yield was found either between the transgenic hybrids or as compared to the hybrid controls (Table 7).

TABLE 7

Meta-analysis of yield from hybrid agronomic field trials.

| Field Trial | Hybrid Maize | Yield (Bu/ac) | LSD (p < 0.05) |
|---|---|---|---|
| Year 1 combined SA and US | Control | 180.28 | 6 |
| Year 1 combined SA and US | MON 87419 | 179.01 | 6 |
| Year 1 combined SA and US | EVENT 2 | 184.88 | 6 |
| SA Year 2 | Control | 231.70 | 10 |
| SA Year 2 | MON 87419 | 232.47 | 10 |
| SA Year 2 | EVENT 2 | 225.07 | 10 |
| US Year 2 Tester 1 | Control | 185.80 | 17.40 |
| US Year 2 Tester 1 | MON 87419 | 187.09 | 17.40 |
| US Year 2 Tester 1 | EVENT 2 | 192.28 | 17.40 |
| US Year 2 Tester 2 | Control | 219.12 | 12.83 |
| US Year 2 Tester 2 | MON 87419 | 219.56 | 12.83 |
| US Year 2 Tester 2 | EVENT 2 | 221.22 | 12.83 |
| US Year 2 Tester 3 | Control | 197.62 | 8.66 |
| US Year 2 Tester 3 | MON 87419 | 191.49 | 8.66 |
| US Year 2 Tester 3 | EVENT 2 | 195.48 | 8.66 |

Inbred efficacy field trials were conducted using a randomized complete block design at 6 locations, 1 state. In these field trials, the dicamba formulation was Clarity 4SL, and the glufosinate formulation was Ignite 280 2.34SL. The herbicide application for the inbred efficacy field trials were glufosinate at 0.8 lb ai/ac and dicamba at 2.0 lbs ae/ac applied at VE-V2 followed by glufosinate at 0.8 lb ai/ac and dicamba at 2.0 lbs ae/ac applied at V8. At the end of the season, yield was measured. For each of the trials, a statistical difference in inbred efficacy yield was found when comparing inbred yield harvested from these trials from transgenic maize containing either of the two events (Table 8). These data indicate the superior performance of transgenic maize containing the maize MON 87419 event.

TABLE 8

Meta-analysis of yield from inbred efficacy field trials.

| Field Trial | Inbred Maize | Yield (Bu/ac) | LSD (p < 0.05) |
|---|---|---|---|
| year 2 US Inbred | MON 87419 | 110.95 | 7 |
| year 2 US Inbred | EVENT 2 | 98.89 | 7 |

Inbred agronomic field trials were run during the same season with the US Year 1 efficacy field trials, SA Year 1 efficacy field trials, and US Year 2 efficacy field trials (11 locations, 1 state). The plots were set up in randomized complete block design conducted at multiple locations, and the trials included controls of a comparable inbred to the transgenic inbred lines. Meta-analysis across the multi-season, multi-location inbred agronomic field trials was conducted comparing yield for the paired control and the transgenic inbreds generated using either of the two events. No statistical difference in inbred agronomic yield was found between the control and transgenic maize containing the MON 87419 event (Table 9). In contrast, there was a statistically significant decrease in yield in transgenic maize containing the event 2 when compared to either control or transgenic maize containing the MON 87419 event. These data further indicated the superior performance of transgenic maize containing the maize MON 87419 event.

TABLE 9

Meta-analysis of yield from inbred agronomic field trials.

| Field Trial | Inbred Maize | Total (Bu/ac) | LSD (p < 0.05) |
|---|---|---|---|
| year 1 US Inbred | Control | 65.87 | 31 |
| year 1 US Inbred | MON 87419 | 60.33 | 31 |
| year 1 US Inbred | EVENT 2 | 43.10 | 31 |
| year 2 SA Inbred | Control | 95.88 | 7 |
| year 2 SA Inbred | MON 87419 | 98.77 | 7 |
| year 2 SA Inbred | EVENT 2 | 75.85 | 7 |
| year 2 US Inbred | Control | 108.90 | 6 |
| year 2 US Inbred | MON 87419 | 109.22 | 6 |
| year 2 US Inbred | EVENT 2 | 96.88 | 6 |

Example 2: Characterization of the DNA Sequence of the Maize MON 87419 Event

This example describes the extensive molecular characterization that was conducted on the maize MON 87419 event. The transgene insert of the maize MON 87419 event contains, from the 5' to 3' orientation: (i) the promoter (P-ANDge.Ubq1), leader, and intron (L-I-ANDge.Ubq1) of the ubiquitin gene (Ubq) from *Andropogon gerardii*; operably linked to the pat gene from *Streptomyces viridochromogenes* (CR-STRvi.pat) that encodes a phosphinothricin N-acetyltransferase (PAT) that confers tolerance to glufosinate herbicide; operably linked to the polyadenylation signal (also known as a terminator that directs polyadenylation of mRNA) from the RA5B precursor gene of *Oryza sativa* (T-Os.Ara5) and (ii) the promoter for the full length transcript of Peanut Chlorotic Streak Virus with a duplicated enhancer region (PClSV); operably linked to the leader of the light harvesting complex b1 gene from *Triticum aestivum* (L-Ta.Lhcb1); operably linked to the first intron from the actin 1 gene from *Oryza sativa* (I-Os.Act1); operably linked to the N-terminal chloroplast transit peptide from the *Petunia x hybrida* 5-enolpyruvylshikimate-3-phosphate synthase gene (TS-Ph.ShkG-CTP4); operably linked to the dmo gene *Stenotrophomonas maltophilia* optimized for monocot expression (CR-STEma.DMO) that encodes a dicamba monooxygenase (DMO) that confers tolerance to dicamba herbicide; operably linked to the heat shock protein 17 polyadenylation signal from *Triticum aestivum* (T-Ta.Hsp17). The 5' end of the transgene insert was flanked by the Right border of *Agrobacterium tumifaciens* and the 3' end of the transgene insert was flanked by the Left border of *Agrobacterium tumifaciens*.

Southern blot analysis was conducted to confirm that transgenic maize containing the maize MON 87419 event contained a single, intact copy of the entire transgene insert without any vector backbone. Flank sequences were isolated from both the 5' and 3' ends of the insert, and the respective junctions were determined using inverse PCR and/or genome walking techniques. The chromosomal location of the insert of the maize MON 87419 event was determined using inverse PCR to amplify genomic DNA outside of the site of interest. The flank sequences for the maize MON 87419 event were mapped to the known maize genome physical assembly and the maize MON 87419 event was confirmed to not be within any known genes. This sequence information was used to design event specific endpoint TAQMAN® assays to identify the presence of the maize MON 87419 event in a sample. The insertion site sequence information was also used for bioinformatics analysis of the chromosomal location of the event. Insertion site integrity was determined by PCR across the wild-type allele using primers specific to the flanking regions of the maize MON 87419 event. The wild-type insertion site was used to map to the maize reference genome the unique site of transgene integration for the maize MON 87419 event. To ensure that no alterations or mutations were introduced to any region of the transgene during transformation, the entire transgene insert of the maize MON 87419 even was isolated from the plant and sequenced.

N-terminal protein sequencing of the expressed PAT and DMO proteins was performed using immunopurified protein extracts from transgenic maize grain containing the maize MON 87419 event. This sequence was then used to confirm the authentic N-terminal amino acid sequence. Western analysis was conducted on protein extracts from grain of transgenic maize containing the maize MON 87419 event. This confirmed that a single expected-sized protein was being produced for PAT and for DMO, respectively. ELISAs were developed to determine protein levels in various transgenic maize tissue types (leaf, seed, roots, and pollen) for the PAT or DMO protein expressed from the maize MON 87419 event. Northern analysis was conducted on poly-A RNA isolated from grain of transgenic maize containing the maize MON 87419 event. This confirmed the transcript size and number for the pat and dmo mRNA products. RNA expression levels were also measured by real-time PCR using samples from transgenic maize containing the maize MON 87419 event.

Example 3: Event Specific Endpoint TAQMAN® Assays

This example describes an event specific endpoint TAQMAN® thermal amplification method developed to identify transgenic maize containing the maize MON 87419 event in a sample. The DNA primers used in the endpoint assay are primers SQ26644 (SEQ ID NO:11), SQ26645 (SEQ ID NO:12), and 6-FAM™ labeled probe PB11207 (SEQ ID NO:13). 6-FAM™ is a fluorescent dye product of Applied Biosystems (Foster City, Calif.) attached to the DNA probe. For TAQMAN® MGB™ probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence. SQ26644 and SQ26645 when used with these reaction methods and PB11207 produce a DNA amplicon that is diagnostic for the maize MON 87419 event. The controls for this analysis should include a positive control containing the maize MON 87419 event, a negative control from non-transgenic maize, and a negative control that contains no template DNA. Additionally, a control for the PCR reaction should optimally include Internal Control Primers and an Internal Control Probe, specific to a single copy gene in the maize genome. These assays are optimized for use with either an Applied Biosystems GeneAmp® PCR System 9700 (run at maximum speed) or MJ Research DNA Engine PTC-225 thermal cycler, but other equipment may be used.

An example of conditions useful with Endpoint TAQMAN® assay method useful for detection of the maize MON 87419 event is as follows. Step 1: 18 megohm water adjusted for final volume of 10 µl. Step 2: 5.0 µl of 2× Universal Master Mix (dNTPs, enzyme, buffer) to a 1× final concentration. Step 3: 0.5 µl Event Primer-1 (SQ26644) and Event Primer-2 (SQ26645). Mix (resuspended in 18 megohm water to a concentration of 20 uM for each primer) to 1.0 µM final concentration (for example in a microcentrifuge tube, the following should be added to achieve 500 µl at a final concentration of 20 uM: 100 µl of Primer SQ26644 at a concentration of 100 µM; 100 µl of Primer SQ26645 at a concentration of 100 µM; 300 µl of 18 megohm water). Step 4: 0.2 µl Event 6-FAM™ MGB Probe PB11207 (10 uM) (resuspended in 18 megohm water to a concentration of 10 µM to 0.2 µM final concentration. Step 5: 0.5 µl Internal Control Primer-1 and Internal Control Primer-2 Mix (resuspended in 18 megohm water to a concentration of 20 µM for each primer) to 1.0 µM final concentration. Step 6: 0.2 µl Internal Control VIC™ Probe (10 uM) to 0.2 µM final concentration (resuspended in 18 megohm water to a concentration of 10 µM). Step 7: 3.0 µl Extracted DNA (template) for each sample with one each of the following comprising 1. Leaf Samples to be analyzed; 2. Negative control (non-transgenic DNA); 3. Negative water control (no template); 4. Positive control transgenic maize containing the maize MON 87419 event DNA. Step 8: Thermocycler Conditions as follows: One Cycle at 50° C. for 2 minutes; One Cycle at 95° C. for 10 minutes; Ten Cycles of 95° C. for 15 seconds then 64° C. for 1 minute with (−1° C./cycle); Thirty Cycles of 95° C. for 15 seconds then 54° C. 1 minute, optional additional 10 to 20 cycles (95° C. for 15 seconds then 64° C. for 1 minute (−1° C./cycle) may provide more distinct population separation during EndPoint TaqMan® analysis); final cycle of 10° C.

Example 4: Zygosity Assay

A zygosity assay may be used to determine whether or not a plant comprising the maize MON 87419 event is heterozygous or homozygous for the event or the wild-type allele. An amplification reaction assay can be designed using the sequence information provided herein. For example, such a PCR assay would include design of at least three primers: primer-1, primer-2, and primer-3, where primer-1 is specific to maize genomic DNA on the 3' flank of the maize MON 87419 event; primer-2 is specific to the maize MON 87419 event transgene insert; and primer-3 is specific to the wild-type allele. When used as a primer pair in an amplification reaction, primer-1 with primer-2 will produce a PCR amplicon specific for the maize MON 87419 event. When used as a primer pair in an amplification reaction, primer-1 with primer-3 will produce a PCR amplicon specific for wild-type allele. In a PCR reaction performed on maize genomic DNA, the respective PCR amplicons generated from (primer-1+primer-2) and (primer-1+primer-3) will differ in sequence and size of the amplicon. When the three primers are included in a PCR reaction with DNA extracted from a plant homozygous for the maize MON 87419 event, only the primer-1+primer-2 amplicon will be generated. When the three primers are included in a PCR reaction with DNA extracted from a plant heterozygous for the maize MON 87419 event, both the primer-1+primer-2 amplicon and the primer-1+primer-3 amplicon will be generated. When the three primers are mixed together in a PCR reaction with DNA extracted from a plant that is null for the maize MON 87419 event (that is wild-type), only the primer-1+primer-3 amplicon will be generated.

Another method to determine zygosity of a maize plant for the maize MON 87419 event is an endpoint TAQMAN® thermal amplification reaction. For this type of assay, in addition to primers as described above, the assay would include two fluorescently labeled probes. Probe-1 would be specific for the maize MON 87419 event, and probe-2 would be specific for a maize plant that is null for the maize MON 87419 event (wild-type), and where the two probes contain different fluorescent labels, for example the 6-FAM™-label or VIC™-label. When used in an endpoint TAQMAN® thermal amplification reaction, primer-1+primer-2+probe-1 will produce a first fluorescent signal specific for the maize MON 87419 event. When used in an endpoint TAQMAN® thermal amplification reaction, primer-1+primer-3+probe-2 will produce a second fluorescent signal specific for wild-type maize. When the three primers and two probes are included in an endpoint TAQMAN® thermal amplification reaction with DNA extracted from a plant homozygous for the maize MON 87419 event, only the first fluorescent signal (specific to primer-1+primer-2+probe-1) will be generated. When the three primers are included in an endpoint TAQ-MAN® thermal amplification reaction with DNA extracted from a plant heterozygous for the maize MON 87419 event, both the first fluorescent signal (specific to primer-1+primer-2+probe-1) and the second fluorescent signal (specific to primer-1+primer-3+probe-2) will be generated. When the three primers are mixed together in an endpoint TAQMAN® thermal amplification reaction with DNA extracted from a plant which is null for the maize MON 87419 event (wild-type), only the second fluorescent signal (specific to primer-1+primer-3+probe-2) will be generated.

Another method to determine zygosity of a plant for the maize MON 87419 event would be Southern analysis. One of skill in art would understand how to design Southern hybridization probe(s) specific for the maize MON 87419 event and a second southern hybridization probe specific for a maize plant which is null for the maize MON 87419 event (wild-type). With Southern analysis, a signal detected only from the first Southern hybridization probe will be indicative of a plant homozygous for the maize MON 87419 event; a signal detected from both the first Southern hybridization probe and the second Southern hybridization probe will be indicative of a plant heterozygous for the maize MON 87419 event; and a signal detected only from the second Southern hybridization probe will be indicative that the DNA was extracted from a plant that is null for the maize MON 87419 event (wild-type).

What is claimed is:

1. A recombinant DNA molecule comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

2. The recombinant DNA molecule of claim 1, wherein the DNA molecule is from a transgenic maize plant or seed comprising the maize MON 87419 event, a representative sample of seed comprising said event having been deposited as ATCC Accession No. PTA-120860.

3. The recombinant DNA molecule of claim 1, wherein the DNA molecule comprises SEQ ID NO:1 and SEQ ID NO:2.

4. The recombinant DNA molecule of claim 1, wherein the DNA molecule is in a maize plant, cell, seed, progeny plant, or plant part from transgenic maize comprising the maize MON 87419 event, a representative sample of seed comprising said event having been deposited as ATCC PTA-120860.

5. A DNA molecule comprising a sufficient length of contiguous DNA sequence of SEQ ID NO:10 to function as a DNA probe that hybridizes under stringent hybridization conditions with a DNA sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, wherein the DNA molecule does not hybridize under the stringent hybridization conditions with a DNA sequence not comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, and wherein said DNA molecule comprises SEQ ID NO:1 or SEQ ID NO:2.

6. A method of detecting the presence of the maize MON 87419 event in a sample of DNA, the method comprising:
   a) contacting the sample with the DNA molecule of claim 5;
   b) subjecting the sample and the DNA molecule to stringent hybridization conditions; and
   c) detecting hybridization of the DNA molecule to a target DNA molecule in the sample,
   wherein the hybridization of the DNA molecule to the target DNA molecule indicates the presence of the maize MON 87419 event in the sample of DNA.

7. A method of detecting the presence of the maize MON 87419 event in a sample of DNA, the method comprising:
   a) contacting the sample with a pair of DNA molecules comprising a first DNA molecule and a second DNA molecule, wherein the first DNA molecule is a fragment of SEQ ID NO:9 and the second DNA molecule is a fragment of the maize genomic DNA of the maize MON 87419 event, and wherein the first and second DNA molecules each comprise a DNA sequence of sufficient length of contiguous nucleotides to function as DNA primers when used together in an amplification reaction with DNA containing the maize MON 87419 event to produce an amplicon diagnostic for the maize MON 87419 event in a sample, wherein said amplicon comprises SEQ ID NO:1 or SEQ ID NO:2;
   b) performing an amplification reaction sufficient to produce a DNA amplicon comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8; and
   c) detecting the presence of the DNA amplicon in the reaction,
   wherein the presence of the DNA amplicon in the reaction indicates the presence of the maize MON 87419 event in the sample of DNA.

8. A DNA detection kit comprising a DNA molecule comprising SEQ ID NO:1 or SEQ ID NO:2.

9. The recombinant DNA molecule of claim 1, wherein the recombinant DNA molecule comprises the nucleotide sequence of SEQ ID NO:1.

10. The recombinant DNA molecule of claim 1, wherein the recombinant DNA molecule comprises the nucleotide sequence of SEQ ID NO:2.

11. The recombinant DNA molecule of claim 1, wherein the recombinant DNA molecule comprises the nucleotide sequence of SEQ ID NO:3.

12. The recombinant DNA molecule of claim 1, wherein the recombinant DNA molecule comprises the nucleotide sequence of SEQ ID NO:4.

13. The recombinant DNA molecule of claim 1, wherein the recombinant DNA molecule comprises the nucleotide sequence of SEQ ID NO:5.

14. The recombinant DNA molecule of claim 1, wherein the recombinant DNA molecule comprises the nucleotide sequence of SEQ ID NO:6.

15. The recombinant DNA molecule of claim 1, wherein the recombinant DNA molecule comprises the nucleotide sequence of SEQ ID NO:7.

16. The recombinant DNA molecule of claim 1, wherein the recombinant DNA molecule comprises the nucleotide sequence of SEQ ID NO:8.

17. The recombinant DNA molecule of claim 1, wherein the recombinant DNA molecule comprises the nucleotide sequence of SEQ ID NO:9.

18. The recombinant DNA molecule of claim 1, wherein the recombinant DNA molecule comprises the nucleotide sequence of SEQ ID NO:10.

* * * * *